(12) United States Patent
Vasievich et al.

(10) Patent No.: US 9,789,129 B2
(45) Date of Patent: Oct. 17, 2017

(54) STIMULATION OF AN IMMUNE RESPONSE BY ENANTIOMERS OF CATIONIC LIPIDS

(75) Inventors: Elizabeth Ann Vasievich, Chapel Hill, NC (US); Weihsu Claire Chen, San Diego, CA (US); Kenya Toney Johnson, Mason, OH (US); Gregory Conn, Lawrenceburg, IN (US); Frank Bedu-Addo, Lawrenceburg, IN (US); Leaf Huang, Durham, NC (US)

(73) Assignee: PDS Biotechnology Corporation, North Brunswisk, NJ (US)

( * ) Notice: Subject to any disclaimer, the term of this patent is extended or adjusted under 35 U.S.C. 154(b) by 750 days.

(21) Appl. No.: 12/988,236

(22) PCT Filed: Apr. 14, 2009

(86) PCT No.: PCT/US2009/040500
§ 371 (c)(1),
(2), (4) Date: Dec. 23, 2010

(87) PCT Pub. No.: WO2009/129227
PCT Pub. Date: Oct. 22, 2009

(65) Prior Publication Data
US 2011/0110972 A1    May 12, 2011

Related U.S. Application Data

(60) Provisional application No. 61/045,837, filed on Apr. 17, 2008.

(51) Int. Cl.
*A61K 45/00*    (2006.01)
*A61K 31/685*    (2006.01)

(52) U.S. Cl.
CPC .................................. *A61K 31/685* (2013.01)

(58) Field of Classification Search
None
See application file for complete search history.

(56) References Cited

U.S. PATENT DOCUMENTS

| 6,419,931 | B1 | 7/2002 | Vitiello et al. |
| 7,303,881 | B2 | 12/2007 | Huang et al. |
| 2006/0008472 | A1 | 1/2006 | Huang et al. |
| 2006/0159738 | A1* | 7/2006 | Graham et al. ............... 424/450 |
| 2008/0014254 | A1 | 1/2008 | Platscher et al. |

(Continued)

FOREIGN PATENT DOCUMENTS

| WO | WO 93/03764 | 3/1993 |
| WO | 00/50006 | 8/2000 |
| WO | 2002/97116 | 12/2002 |

(Continued)

OTHER PUBLICATIONS

Song et al., "Free liposomes enhance the transfection activity of DNA/lipid complexes in vivo by intravenous administration," Biochimica et Biophysica Acta 1372 (pp. 141-150 (1998).*

(Continued)

*Primary Examiner* — Janet L Andres
*Assistant Examiner* — M. Franco Salvoza
(74) *Attorney, Agent, or Firm* — DLA Piper LLP (US)

(57) ABSTRACT

Compositions and methods for treating immune cells and activating immune responses are disclosed. The compositions comprise one or more optically active chiral cationic lipids.

4 Claims, 15 Drawing Sheets

(56) References Cited

U.S. PATENT DOCUMENTS

2009/0017057 A1     1/2009     Chen et al.

FOREIGN PATENT DOCUMENTS

| WO | 2003/011252 | 2/2003 |
|---|---|---|
| WO | WO2008/116078 | 9/2008 |

OTHER PUBLICATIONS

Datta et al., "Effects of increasing hydrophobicity on the physical-chemical and biological properties of a class A amphipathic helical peptide," Journal of Lipid Research vol. 42, pp. 1096-1104 (2001).*
Robinson et al., "Palmitic acid conjugation of a protein antigen enhances major histocompatibility complex class II—restricted presentation to T cells," Immunology 76, pp. 593-598 (1992).*
Yotsumoto et al., "Endosomal Translocation of CpG-Oligodeoxynucleotides Inhibits DNA-PKcs-Dependent IL-10 Production in Macrophages," J Immunol. 180:809-816 (2008).*
Bei et al., "The use of a cationic liposome (DOTAP) mixed with a recombinant tumor-associated antigen to induce responses and protective immunity in mice," J Immunother. 21(2): pp. 159-169 (1998).*
Bei et al., "The use of a cationic liposome formulation (DOTAP) mixed with a recombinant tumor-associated antigen to induce immune responses and protective immunity in mice," J Immunother 21(3): 159-69 (1998)(abstract only).*
Yan et al. "Mechanism of adjuvant activity of cationic liposome: phosphorylation of a MAP kinase, ERK and induction of chemokines," Mol Immunol 44(15): 3672-81 (2007).*
International Search Report and Written Opinion for PCT/US2009/040500, completed May 22, 2009.
Shimizu et al., "Antitumor activity, mitogenicity, and lethal toxicity of chemical synthesized monosaccharide analog of lipid," A. J. Pharmacobiodyn., 1988; 11(7): 512-518.
Chen et al., Cancer Immunology, Immunotherapy; 2008; 57(4):517-530).
Database Registry, Chemical Abstracts Service, Database accession No. 183283-20-7.
Third Office Action dated May 9, 2016, of corresponding Chinese Application No. 20098021761.x, along with an English translation.
Notification of Reasons for Rejection dated Sep. 15, 2015, of corresponding Japanese Application No. 2014-17712, along with an English translation.
Office Action dated Jun. 22, 2017, of corresponding Indian Application No. 7544/DELNP/2010.

* cited by examiner

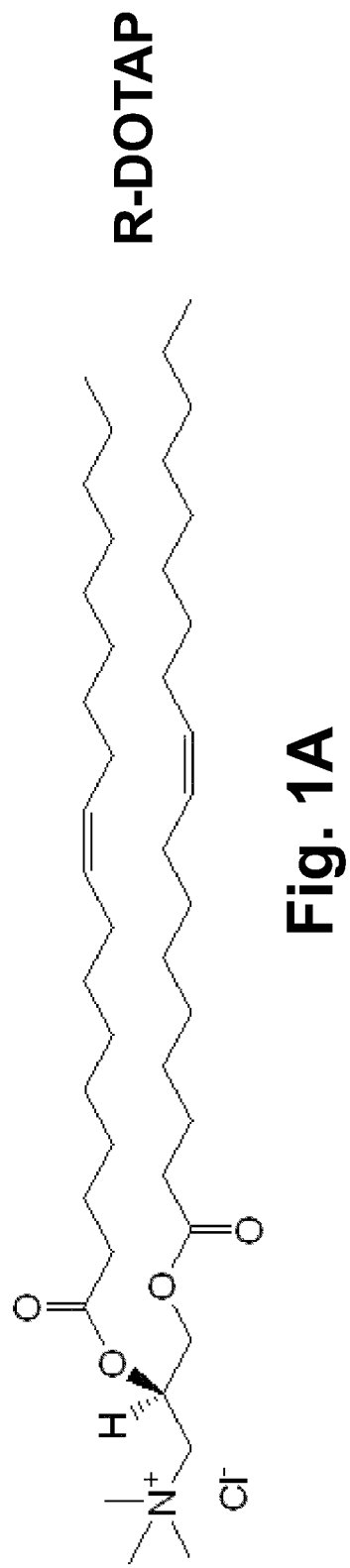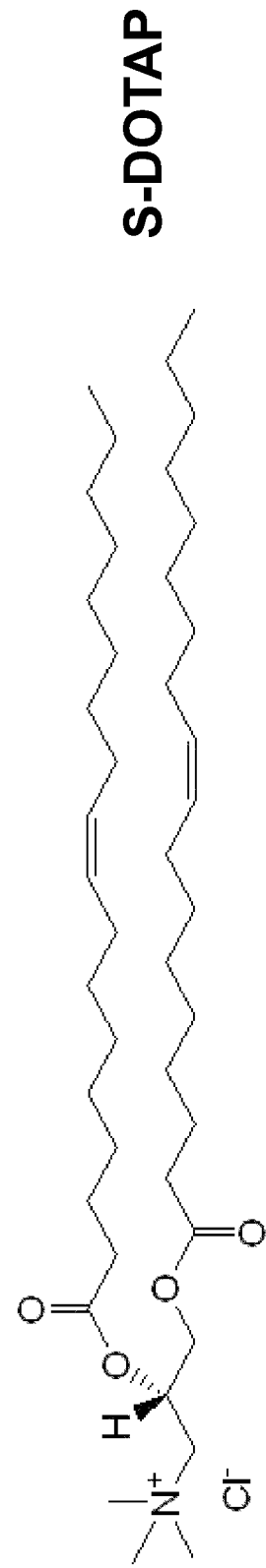

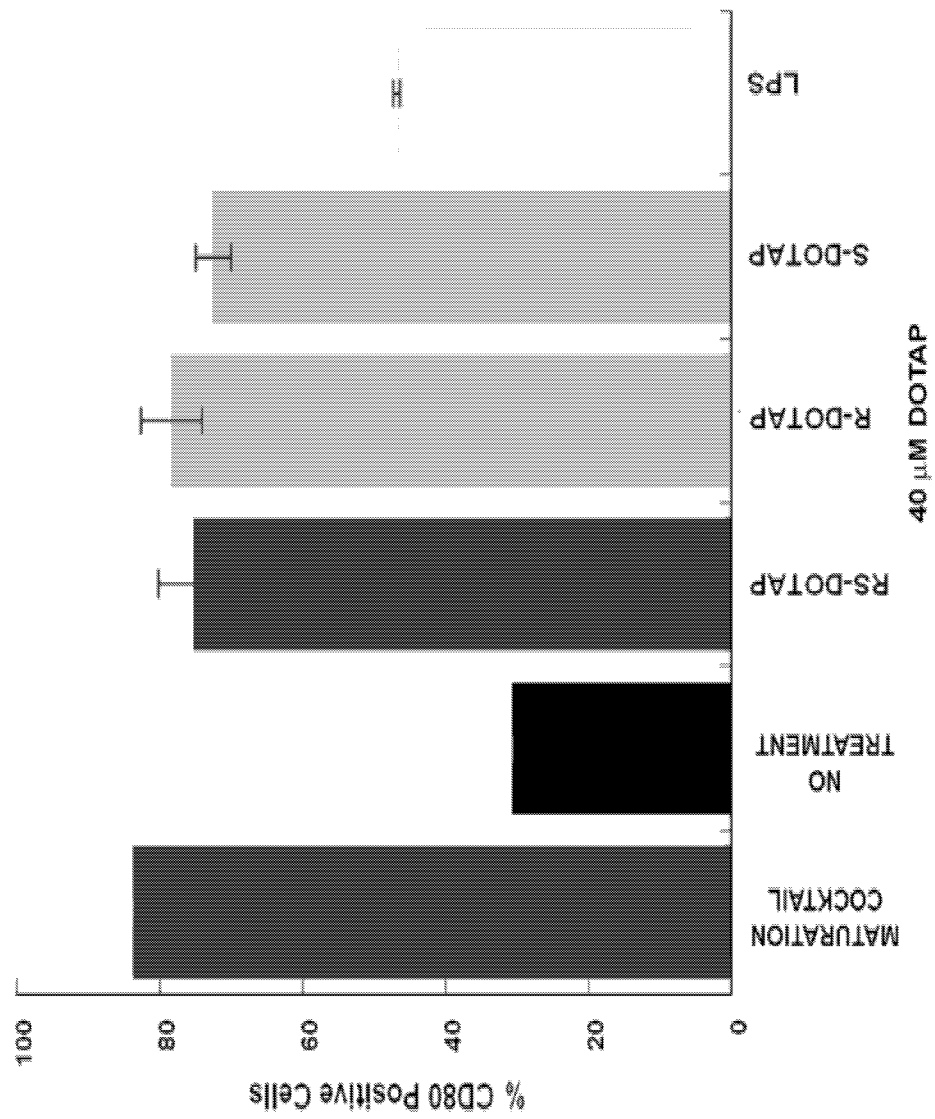

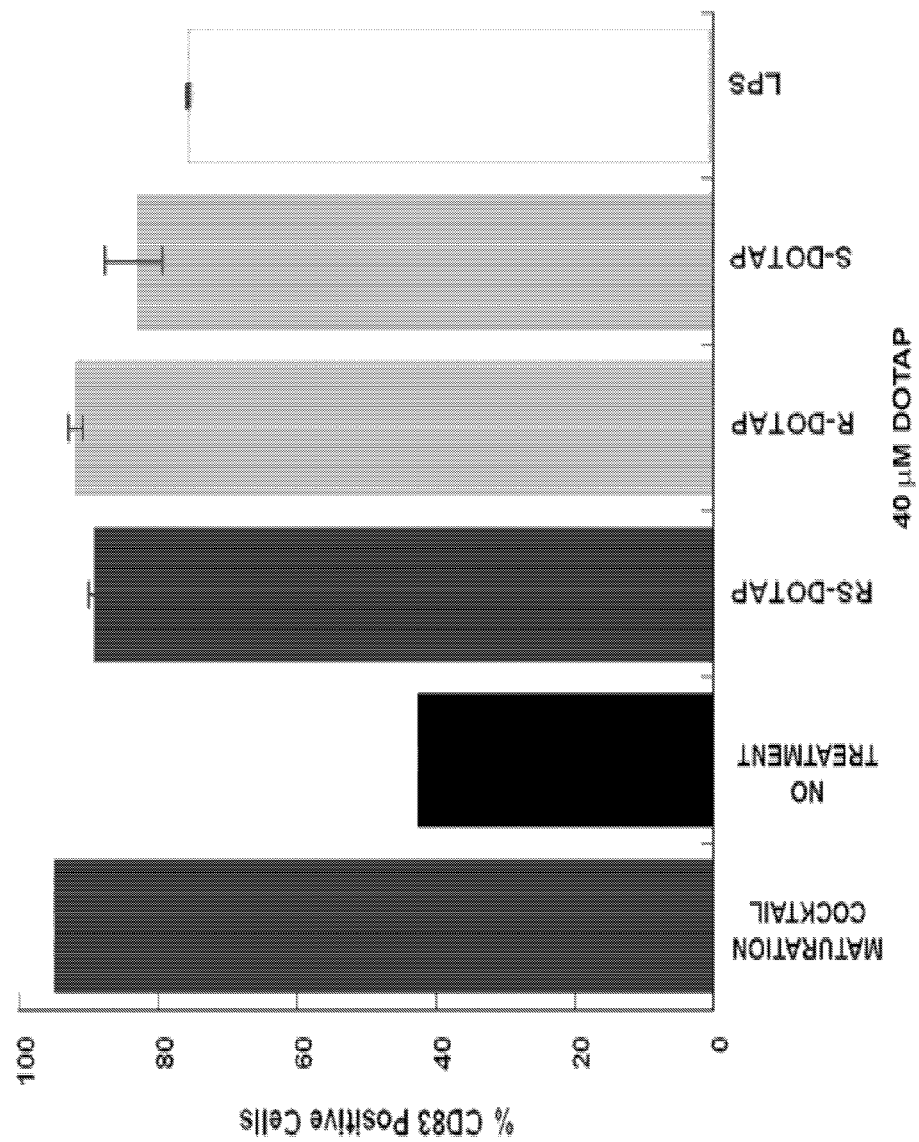

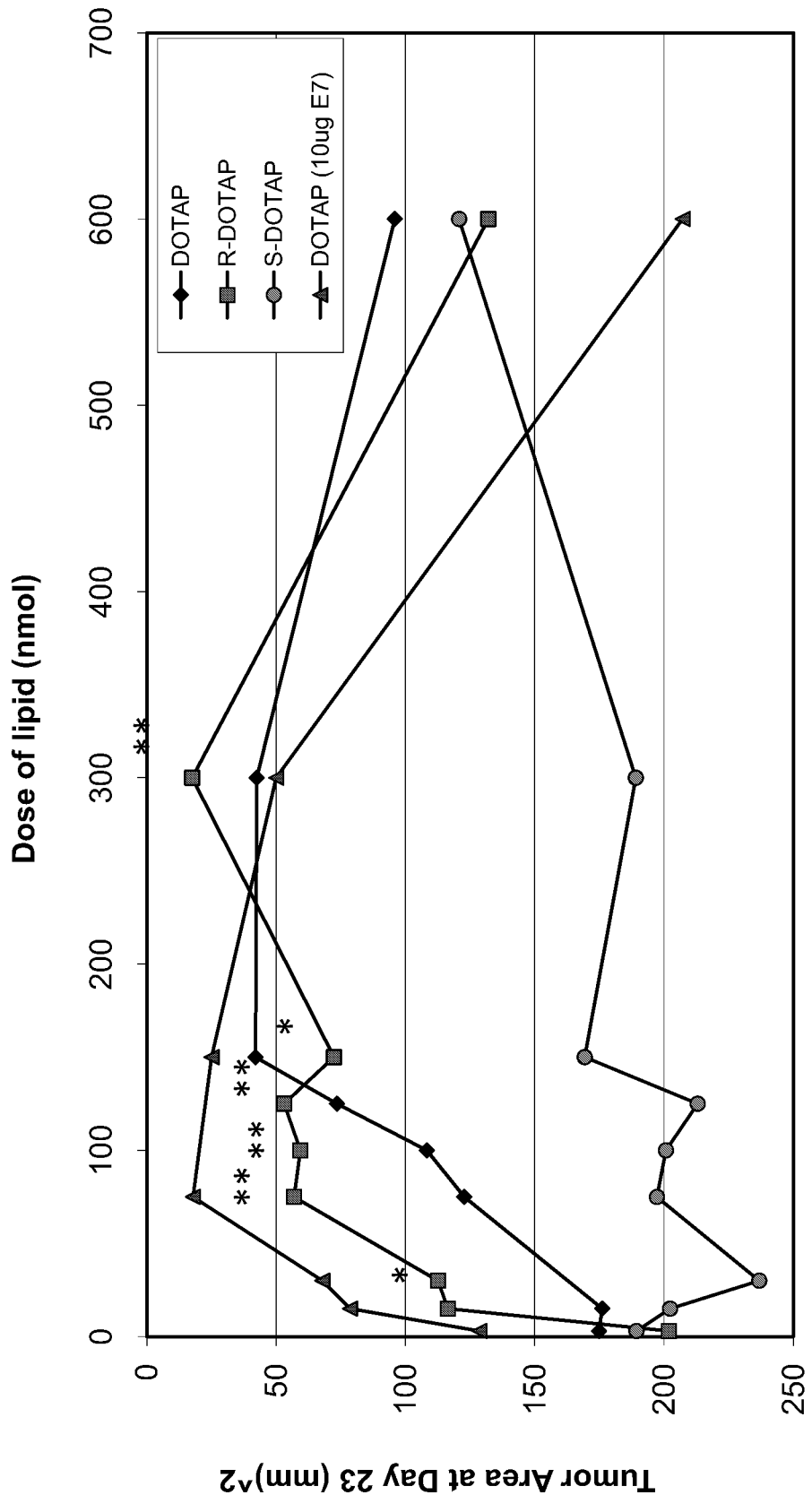

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Human papillovirus subtype 16 E7 oncogene
      tumor-associated antigen MHC class I restricted peptide

<400> SEQUENCE: 1

Tyr Met Leu Asp Leu Gln Pro Glu Thr Thr
1               5                   10
```

STIMULATION OF AN IMMUNE RESPONSE BY ENANTIOMERS OF CATIONIC LIPIDS

CROSS-REFERENCE TO RELATED APPLICATIONS

This application is a U.S. national counterpart application of international application serial no. PCT/US2009/040500 filed Apr. 14, 2009, which claims benefit of U.S. Provisional Application No. 61/045,837, filed on Apr. 17, 2008, the disclosures of which are hereby incorporated by reference herein in their its entirety.

FIELD OF THE INVENTION

The present invention generally relates to stimulating an immune response, and more particularly to the use of the R and S enantiomers of lipids in stimulating immune responses.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Development of safe and effective immunotherapies for human use remains an urgent medical need for patients worldwide. In order to elicit appropriate immune responses, immunologic modifiers ("immunomodifiers") that enhance, direct, or promote an immune response can be used in vaccine design or immunotherapy [Gregoriadis, G., *Immunological adjuvants: a role for liposomes*. Immunol Today 11:89 (1990)]. For example, vaccines may include antigens to stimulate an immune response. However, some potential vaccines that include antigens are weak stimulators of an immune response because the vaccines do not efficiently deliver the antigen to antigen presenting cells ("APC") of the immune system and/or the antigen is weakly immunogenic. Thus, immunotherapies that effectively deliver antigens to APC, and also stimulate the immune system to respond to the antigen, are needed. Immunomodifiers have the potential to function as such an immunotherapy. Such immunotherapies may have these and other benefits. For example, when included as part of a therapeutic vaccine, an immunomodifier should at least (1) improve antigen delivery and/or processing in the APC [Wang, R. F., and Wang, H. Y. *Enhancement of antitumor immunity by prolonging antigen presentation on dendritic cells*. Nat Biotechnol 20:149 (2002)], (2) induce the production of immunomodulatory cytokines that favor the development of immune responses to the vaccine antigen, thus promoting cell mediated immunity, including cytotoxic T-lymphocytes ("CTL"), (3) reduce the number of immunizations or the amount of antigen required for an effective vaccine [Vogel, F. R. *Improving vaccine performance with adjuvants*. Clin Infect Dis 30 Suppl 3:S266 (2000)], (4) increase the biological or immunological half-life of the vaccine antigen, and (5) overcome immune tolerance to antigen by inhibiting immune suppressive factors [Baecher-Allan, C., and Anderson, D. E. *Immune regulation in tumor-bearing hosts*. Curt Opin Immunol 18:214 (2006)].

Presently, the primary class of agents used to enhance the efficacy of antigens, such as peptide or protein antigens, in eliciting an immune response are adjuvants such as water-in-oil emulsions, alum, and other chemicals which enhance antigen responses; however, these adjuvants are not immunomodifiers, as described above, because they have no direct immunomodulatory effects themselves [Vogel, F. R., and Powell, M. F. *A compendium of vaccine adjuvants and excipients*, Pharm Biotechnol 6:141 (1995)]. Several such adjuvants are available for use in animals and some of them have been tested in clinical trials. In addition to traditional adjuvants such as the aluminum salts, products such as influenza virosomes [Gluck, R., and Walti, E. 2000. *Biophysical validation of Epaxal Berna, a hepatitis A vaccine adjuvanted with immunopotentiating reconstituted influenza virosomes (IRIV)*. Dev Biol (Basel) 103:189 (2000)], and Chiron's MF59 [Kahn, J. O., et al. *Clinical and immunologic responses to human immunodeficiency virus (HIV) type ISF2 gp120 subunit vaccine combined with MF59 adjuvant with or without muramyl tripeptide dipahnitoyl phosphatidylethanolamine in non-HIV-infected human volunteers*. J Infect Dis 170:1288 (1994)], which have intrinsic immune effects, are being marketed. For example, MF59, which is a submicron emulsion based adjuvant, is internalized by dendritic cells [Dupuis, M., et al., *Dendritic cells internalize vaccine adjuvant after intramuscular injection*. Cell Immunol 186: 1.8 (1998)]. However, according to clinical trial reports on HSV and influenza vaccines [Jones, C. A., and Cunningham, A. L. *Vaccination strategies to prevent genital herpes and neonatal herpes simplex virus (HSV) disease*. Herpes 11:12 (2004); Minutello, M. et al., *Safety and immunogenicity of an inactivated subunit influenza virus vaccine combined with MF59 adjuvant emulsion in elderly subjects, immunized for three consecutive influenza seasons*. Vaccine 17:99 (1999)], evidence from animal models suggests that the MF59 adjuvant enhances production of neutralizing antibodies rather than enhancing T-cell responses. Thus, new methods of stimulating cell mediated immune responses are needed.

Further, as mentioned above, some antigens are weak stimulators of an immune response. Thus, in addition to co-administering antigen with substances that stimulate immune responses, as described above, a weakly immunogenic antigen can be modified to increase its immunogenicity. For example, a weakly immunogenic antigen can be coupled to immunogenic peptides, polysaccharides, or lipids to increase its immunogenicity. However, simply coupling weakly immunogenic antigens to these types of compounds may not be sufficient to elicit an immune response. For example, the resulting immune response may be directed to immunogenic epitopes on the coupled compound and not the weak antigen, or the coupled antigen may not be efficiently delivered to APC of the immune system. Thus, additional methods are needed to stimulate immune responses to antigens that are weakly immunogenic.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

This invention is directed to the chirality of cationic lipids and the use of the R and S enantiomers of cationic lipids, which under certain dose and composition conditions act as a novel class of immune-stimulants, to (1) effectively present or deliver an antigen to the immune system and (2) stimulate the immune system to respond to the antigen.

Liposomes have been extensively used for delivering small molecular weight drugs, plasmid DNA, oligonucleotides, proteins, and peptides. Vaccines using liposomal vehicles as nonviral antigen carriers are preferable compared to traditional immunizations using live attenuated vaccines or viral vectors such as vaccinia or influenza virus. U.S. patent application Ser. No. 12/049,957, assigned to the assignee of the present application, discloses simple yet effective lipid-based immunotherapies, including a cationic lipid/antigen complex, which has two molecules, a cationic lipid and an antigen, and the effects of the lipid dose on the resulting immune response. The reported results demonstrate that the cationic liposome complexed with an antigen serves to stimulate immune responses and initiate dendritic cell (an APC) interaction with T-cells.

In the present invention, additional studies performed with the two enantiomers of a selected cationic lipid have led to the discovery that differences exist in the ability of the R and S enantiomers of the cationic lipids to act as potent immune activators under various conditions. In combination with an antigen, the cationic lipid/antigen complex containing the R enantiomer, under various dose conditions (including low dose conditions), induces strong immune responses specific to the antigen formulated in the complex and results in tumor regression. Complexes consisting of S-DOTAP and the antigen however were able to induce only limited tumor regression, and not at all doses at which R-DOTAP was effective. Both enantiomers of DOTAP are however equally effective at inducing maturation and activation of dendritic cells, which is the first step in inducing a cellular immune response.

Thus, one aspect of the invention provides a composition of at least one enantiomer of a cationic lipid in a dose sufficient to induce an immune response in a subject.

Another aspect of the invention provides a method of inducing an immune response in a subject by administering a specific enantiomer or a mixture of enantiomers of a cationic lipid to the subject.

Another aspect of the invention provides a composition of an R or S enantiomer of a cationic lipid in a dose sufficient to induce an immune response in a subject.

Additional aspects of the invention involve the addition of at least one antigen to the R or S enantiomer to form a cationic lipid/antigen complex in which case the immune response is antigen-specific.

BRIEF DESCRIPTION OF THE DRAWINGS

Various features, aspects, and advantages of the present invention will become better understood when the following detailed description is read with reference to the accompanying figures, wherein:

FIGS. 1A and 1B depict chirality of 1,2-dioleoyl-3-trimethylammoninum propane ("DOTAP").

FIG. 2 is a graph depicting activation of human dendritic cells resulting in expression of the co-stimulatory molecule CD 80 by R-DOTAP, S-DOTAP and the racemic mixture RS-DOTAP.

FIG. 3 is a graph depicting activation of human dendritic cells resulting in expression of the co-stimulatory molecule CD 83 by R-DOTAP, S-DOTAP and the racemic mixture RS-DOTAP

FIG. 15 is a graph depicting the lipid dose response effects of the racemic mixture of DOTAP, R-DOTAP and S-DOTAP on the in vivo anti-tumor immune response of the cationic lipid/antigen complex with antigen dose of 20 µg. The effect of antigen dose is also demonstrated with the racemic mixture of DOTAP. R-DOTAP compared to S-DOTAP: *$p<0.05$, **0.01, n=5-6.

DETAILED DESCRIPTION

Figure 4:
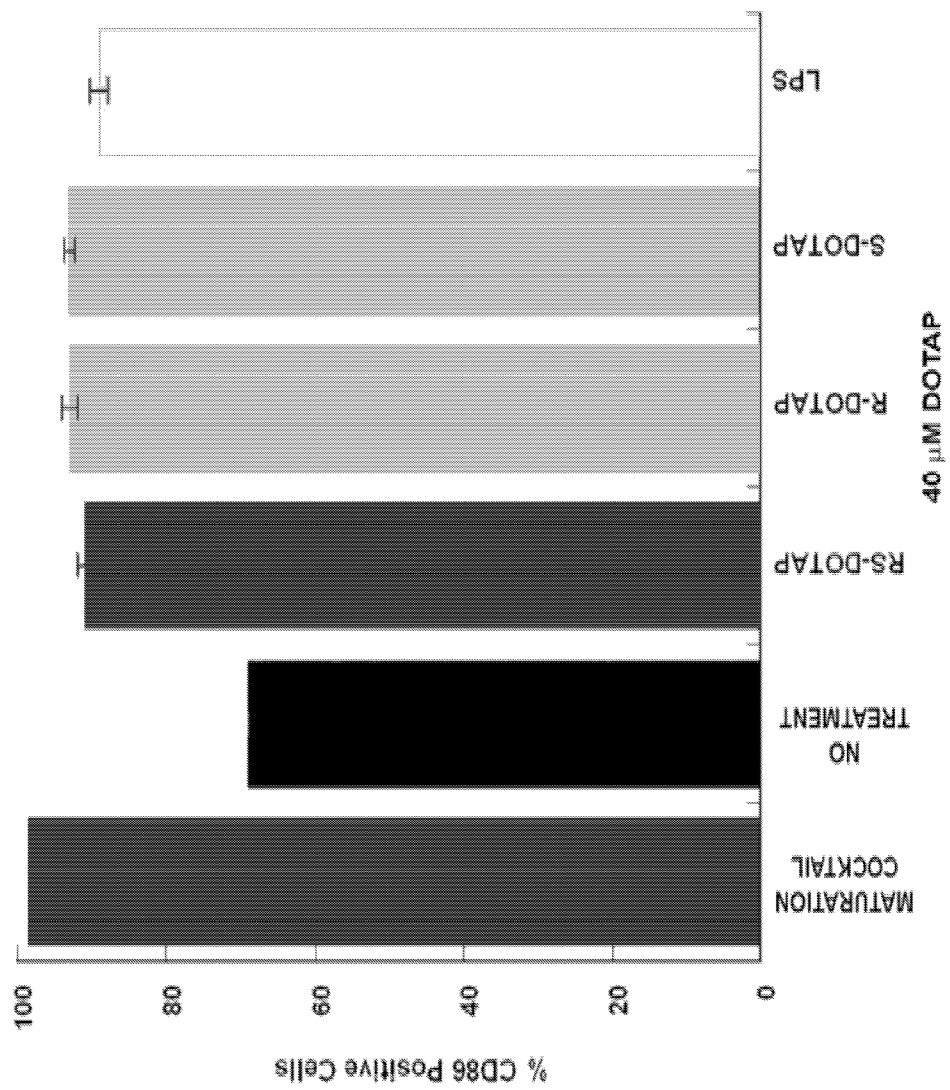
FIG. 4 is a graph depicting activation of human dendritic cells resulting in expression of the co-stimulatory molecule CD 86 by R-DOTAP, S-DOTAP and the racemic mixture RS-DOTAP
Figure 5:
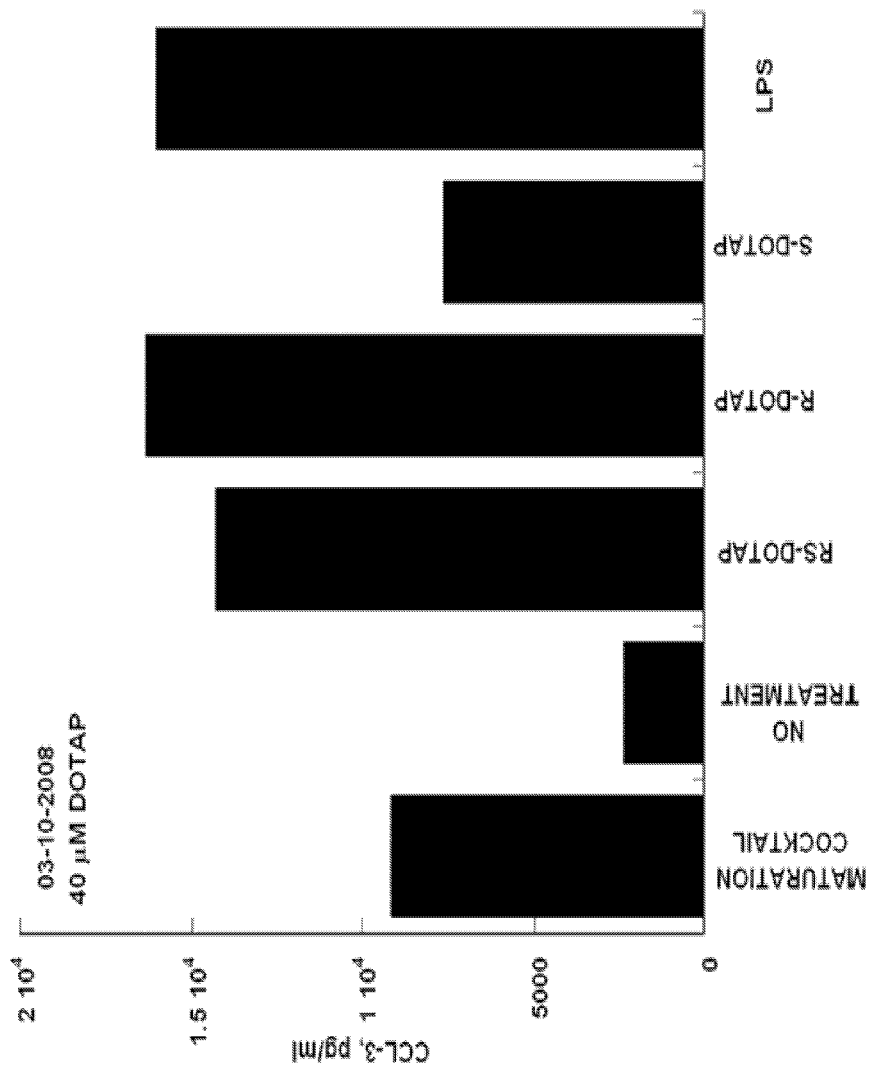
FIG. 5 is a graph depicting stimulation of human dendritic cells resulting in production of the chemokine CCL-3 by R-DOTAP, S-DOTAP and the racemic mixture RS-DOTAP
Figure 6:
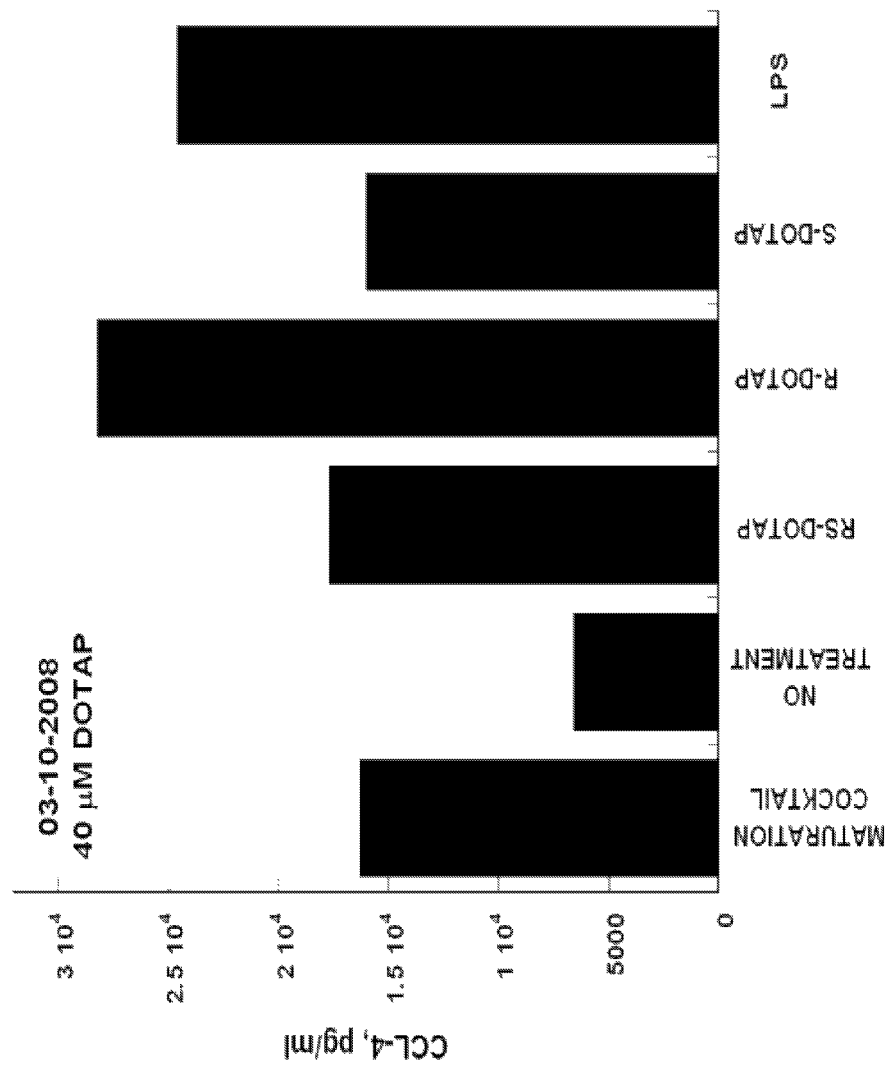
FIG. 6 is a graph depicting stimulation of human dendritic cells resulting in production of the chemokine CCL-4 by R-DOTAP, S-DOTAP and the racemic mixture RS-DOTAP
Figure 7:
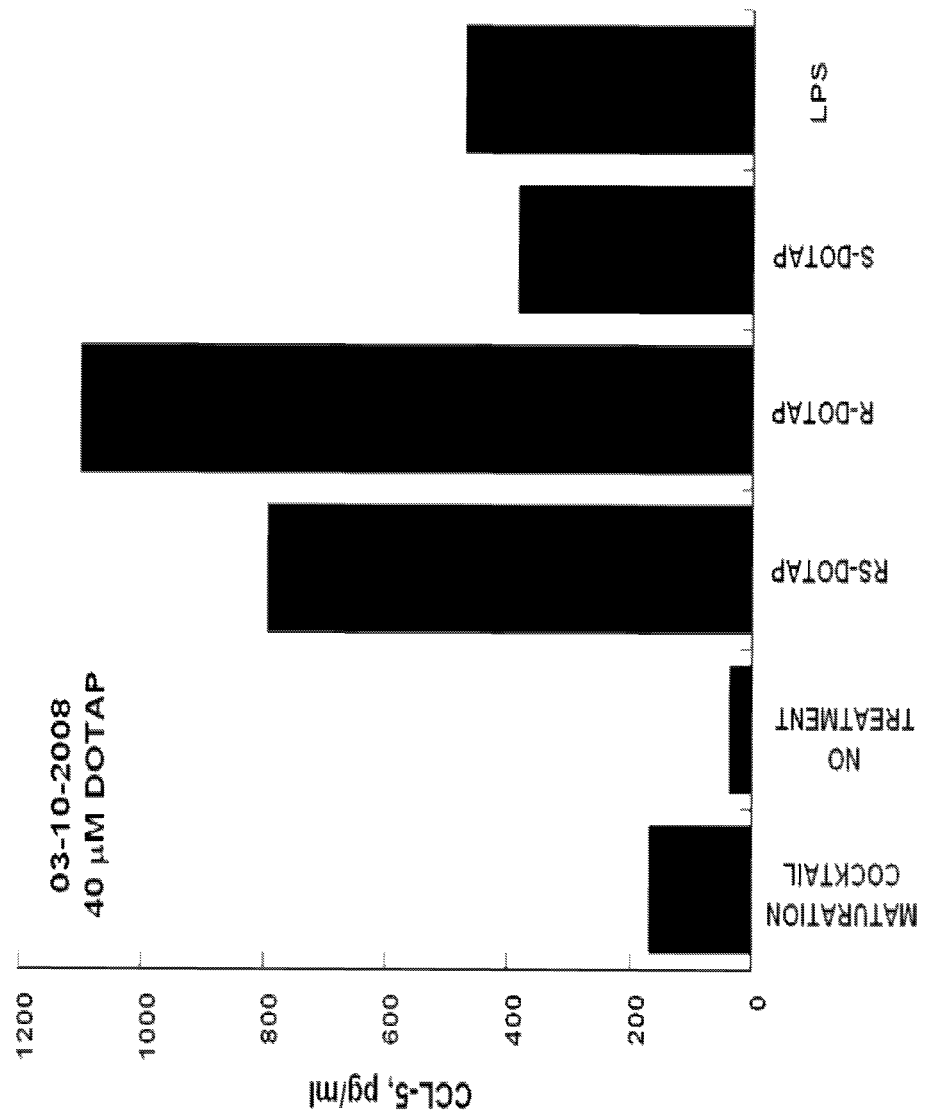
FIG. 7 is a graph depicting stimulation of human dendritic cells resulting in production of the chemokine CCL-5 by R-DOTAP, S-DOTAP and the racemic mixture RS-DOTAP
Figure 8:
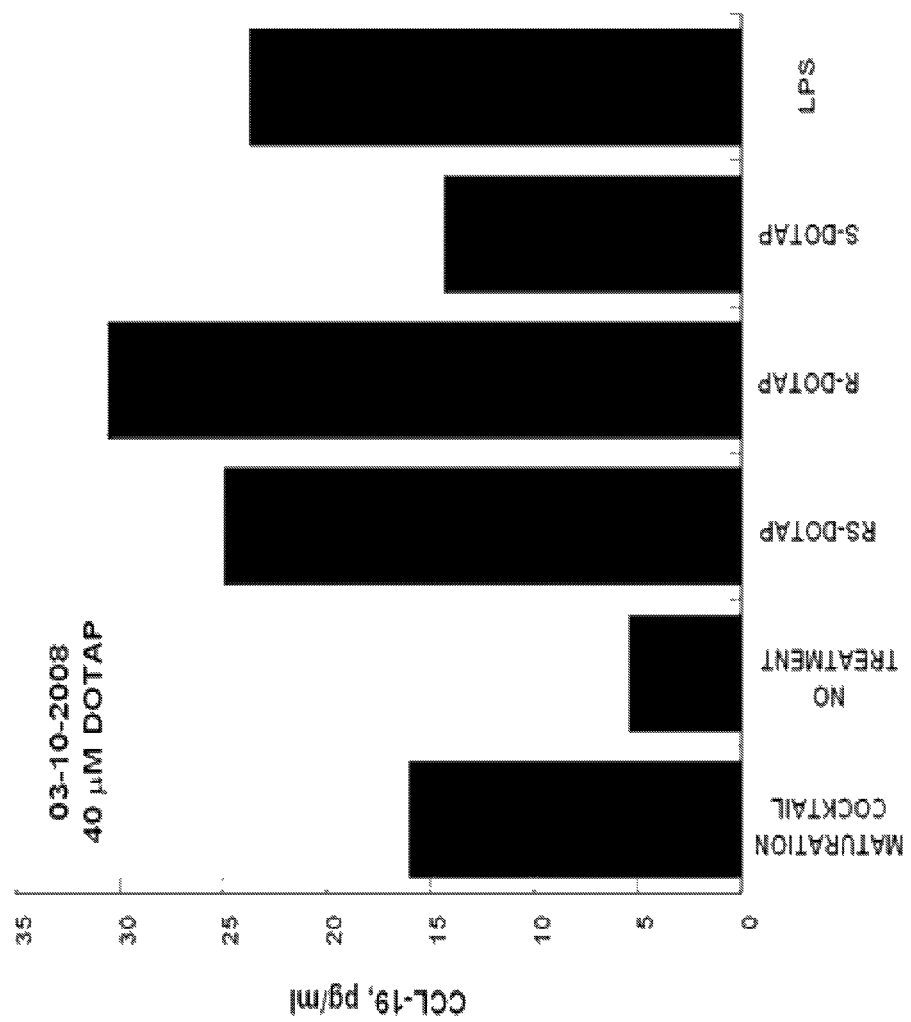
FIG. 8 is a graph depicting stimulation of human dendritic cells resulting in production of the chemokine CCL-19 by R-DOTAP, S-DOTAP and the racemic mixture RS-DOTAP.
Figure 9:
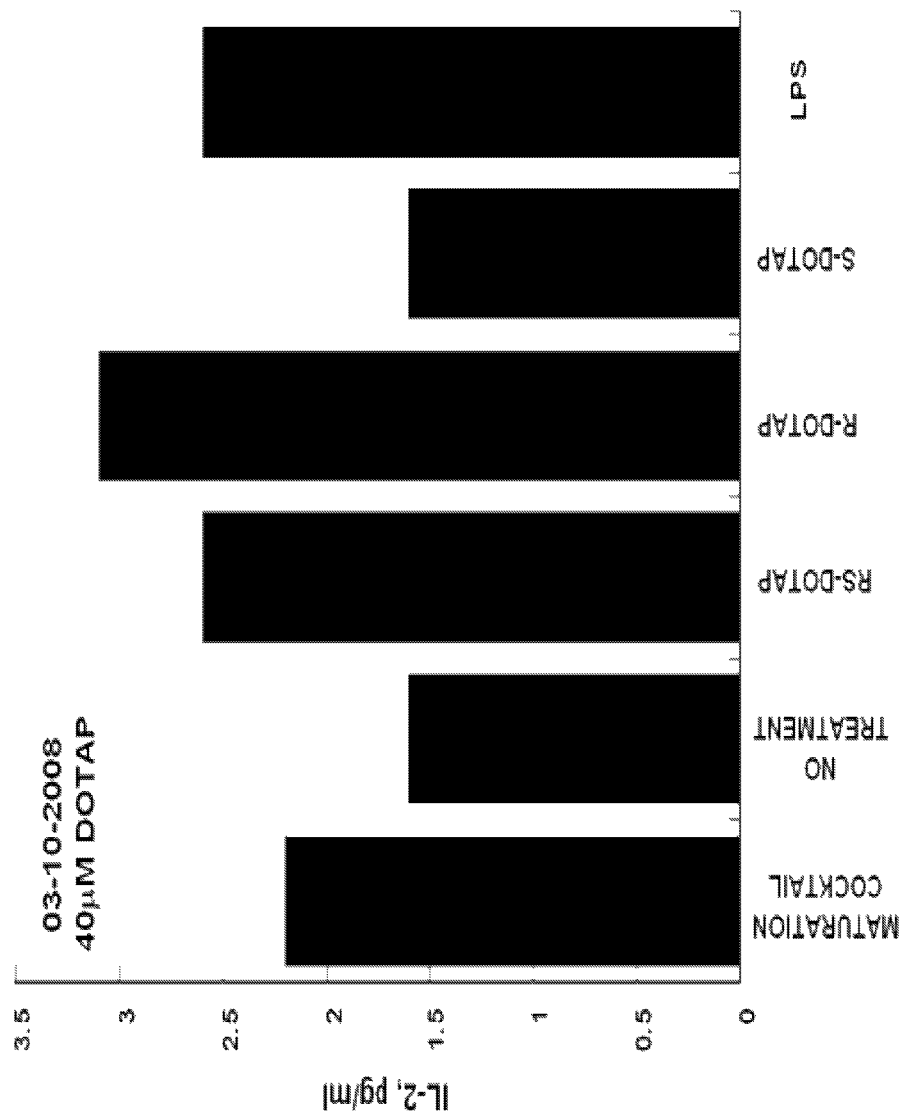
FIG. 9 is a graph depicting stimulation of human dendritic cells resulting in production of the cytokine IL-2 by R-DOTAP, S-DOTAP and the racemic mixture RS-DOTAP.
Figure 10:
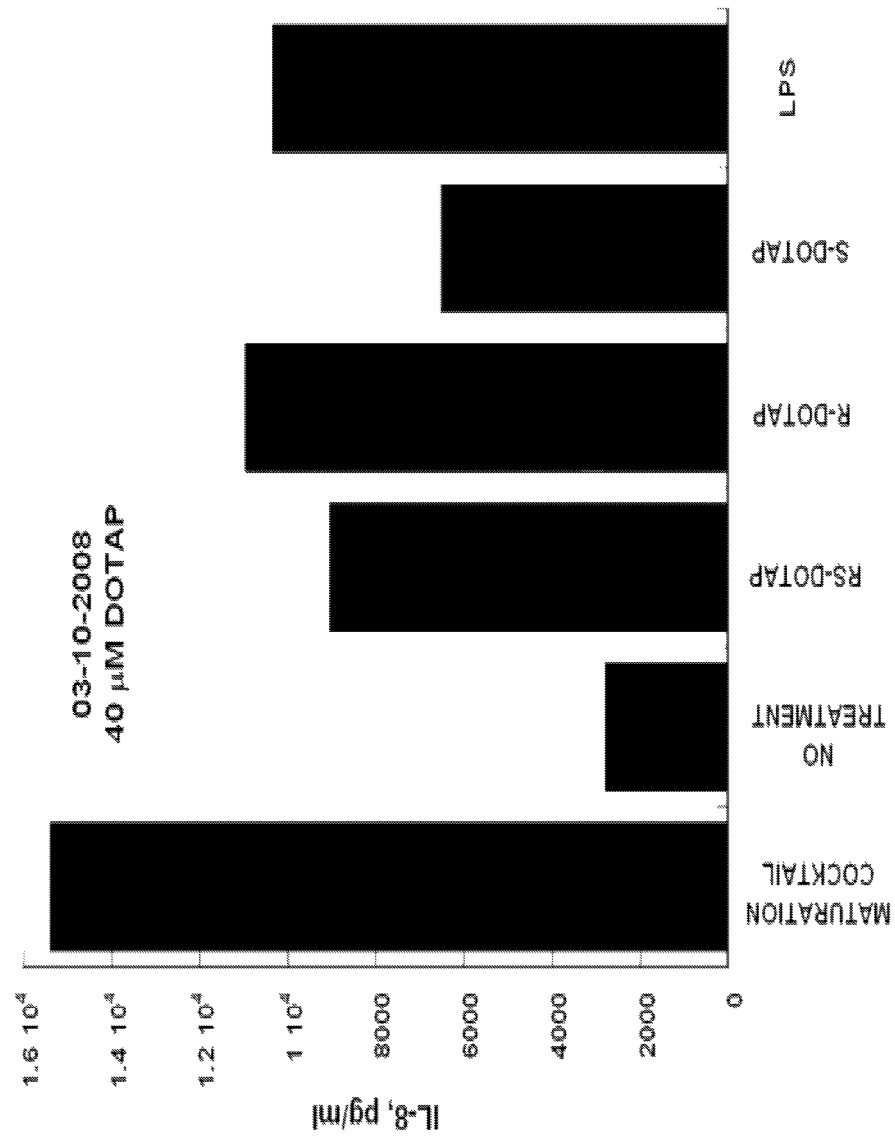
FIG. 10 is a graph depicting stimulation of human dendritic cells resulting in production of the cytokine IL-8 by R-DOTAP, S-DOTAP and the racemic mixture RS-DOTAP.
Figure 11:
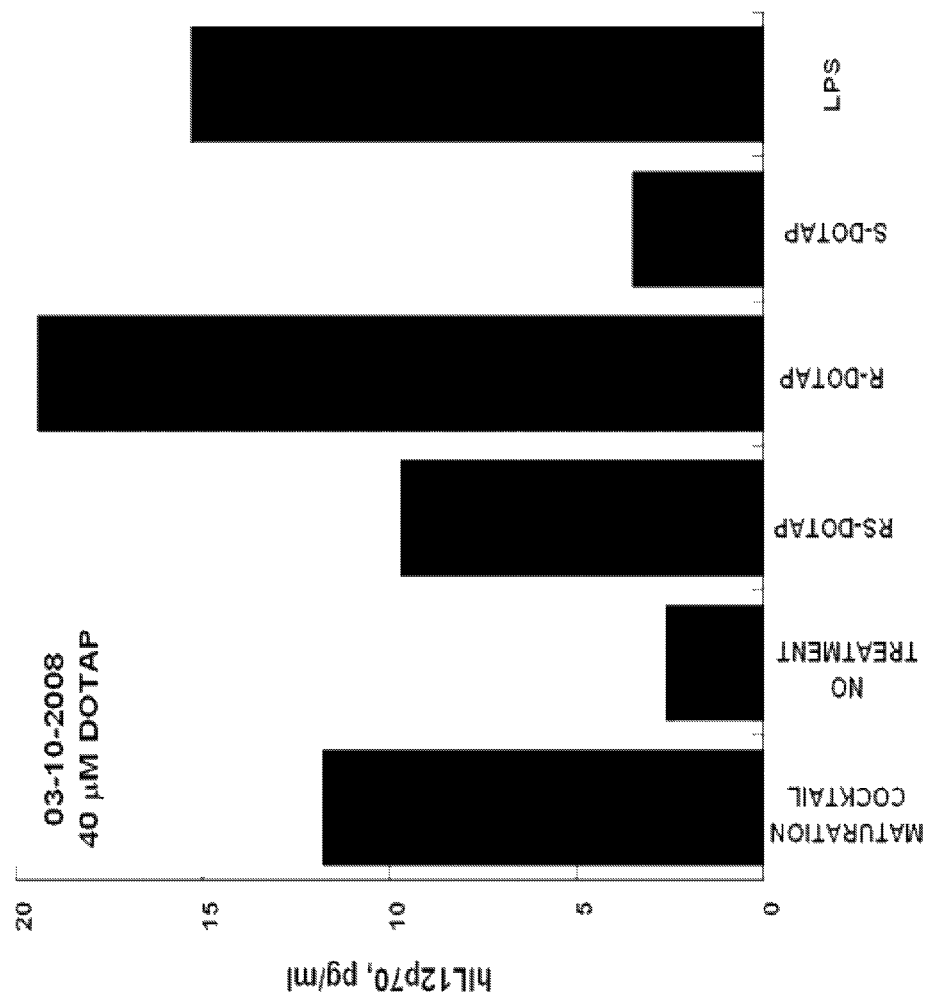
FIG. 11 is a graph depicting stimulation of human dendritic cells resulting in production of the cytokine IL-12 by R-DOTAP, S-DOTAP and the racemic mixture RS-DOTAP.

One or more specific embodiments of the present invention will be described below. In an effort to provide a concise description of these embodiments, all features of an actual implementation may not be described in the specification. It should be appreciated that in the development of any such actual implementation numerous implementation-specific decisions must be made to achieve the developers' specific goals, which may vary from one implementation to another. Moreover, it should be appreciated that such a development effort might be complex and time consuming, but would nevertheless be a routine undertaking for those of ordinary skill having the benefit of this disclosure.

When introducing elements of the present invention (e.g., the exemplary embodiments(s) thereof), the articles "a", "an", "the" and "said" are intended to mean that there are one or more of the elements. The terms "comprising", "including" and "having" are intended to be inclusive and mean that there may be additional elements other than the listed elements.

One aspect of the present invention provides an enantiomer of a cationic lipid to stimulate an immune response in a mammal to prevent or treat disease. The individual chiral lipids can function independently as immunomodulators, in a dose dependent manner, such as for production of chemokines and/or cytokines, by activating various components of the MAP kinase signaling pathway. The dose range that effectively induces an immune response is observed to differ between the R and S enantiomers and also within various mammalian species. For example, in the rodent species the R-enantiomer of DOTAP effectively attenuates tumor growth over a range of about 30 nmole to about 400 nmole. In contrast, the S-enantiomer of DOTAP is effective over this same range of doses in the same species of rodent, though less so than the R-enantiomer. In another aspect, the chiral cationic lipid may be associated with antigens or drugs for presentation to cells of the immune system while simultaneously stimulating a strong antigen-specific immune response. In some aspects of the invention, the antigen is a lipopeptide.

U.S. Pat. No. 7,303,881, incorporated by reference herein in its entirety, discloses that multiple cationic lipids complexed with disease-associated antigens were shown to stimulate a prophylactic immune response that prevented the specific disease (e.g., HPV-positive cancer) and also a therapeutic immune response that killed cells expressing the particular antigen and resulted in an effective treatment of the disease. Presently, studies were performed to further understand the effects of chirality on the immunostimulatory capability of cationic lipids by using the R and S enantiomers of DOTAP. (The R and S enantiomers of DOTAP are shown in FIGS. 1A and 1B). These studies have led to the discovery that individual enantiomers of cationic lipids can function independently as immunodulators to stimulate an immune response with (or without) antigens. Further, when enantiomers of cationic lipids are complexed with an antigen, an antigen specific immune response is generated. The extent of the disease specific immune response differs significantly between the R and S enantiomers of the cationic lipid.

In another aspect, the chiral cationic lipid, at a dose sufficient to stimulate an immune response, is administered in combination with an antigen or antigens. In this case the cationic lipid/antigen combination is capable of generating an immune response that is specific to the antigen(s) delivered in combination with the cationic lipid. The response generated may include production of specific cytotoxic T cells, memory T cells, or B cells resulting in the prevention of, or therapeutic response to, the specific disease associated with the antigen(s).

The chiral cationic lipids of the invention may be in the form of cationic lipid complexes. The cationic lipid complex can take the form of various vesicles such as liposomes, micelles, or emulsions. The cationic lipid complexes may be unilaminar or multilaminar. When an antigen is included, the antigen may be encapsulated in the cationic lipid complex or may be unencapsulated. Encapsulated is understood to mean that the antigen may be contained within the internal space of the complex and/or incorporated into the lipid walls of the complex.

Another aspect of the invention relates to a method for producing these complexes, wherein the method may optionally include the step of purifying these formulations from excess individual components.

In certain embodiments, the cationic lipid complexes have a net positive charge and/or a positively charged surface at pH 6.0-8.0.

The optional "antigen" which may be included with cationic lipid complexes of the invention may be nucleic acids, peptides, lipopeptides, proteins, lipoproteins, polysaccharides, and other macromolecules which may be complexed directly with cationic lipids. However, cationic drugs (e.g., large cationic protein) can be directly complexed with an anionic lipid or sequentially complexed first with anionic lipid or polymer followed by the chiral cationic lipid. The use of this process permits delivery of positive or neutral charged drugs to cells by the complexes of the present invention.

One aspect of the present invention involves the use of the chiral cationic lipid complexes to activate dendritic cells and also to stimulate the production of chemokines and cytokines. Chemokines and cytokines are important regulators of immune responses. Chemokines were originally identified as potent chemoattractants for inflammatory cells including neutrophils, eosinophils, and monocytes/macrophages. Subsequent studies have revealed that chemokines have profound effects on immune reactions by regulating the trafficking of dendritic cells and other lymphocytes into lymphoid organs. Dendritic cells are migratory cells that sample antigens in the tissue, migrate to the draining lymph nodes and mature to stimulate the T cell response. CCL2, a member of the CC chemokines was originally identified as a chemotactic and activating factor for monocytes/macrophages. Subsequent studies showed that it can also affect the function of T cells, natural killer cells, and neutrophils. Further exploration found that CCL2 was the most potent activator of CD8-cytotoxic T lymphocytes ("CTL") activity, when in the presence of the Th1 cytokines, interleukin-12 ("IL-12") and interferon-γ ("IFN-γ"). This can be explained by a positive bidirectional interaction between CCL2 and IFN-γ systems. An absence of either the cytokine or chemokine may interfere with Th1 polarization and subsequent specific tumor immunity generation. Another CC chemokine, CCL-4, has also been shown to recruit and expand dendritic cells in vivo and potentiate the immunogenicity of plasmid DNA vaccines. Recently, it has been shown that chemokines enhance immunity by guiding naïve CD8+ T cells to sites of CD4+ T cell-dendritic cell interaction and promote memory CD8+ T cell generation. A few examples of chemokines that may be stimulated by the cationic lipid complexes of the present invention are CCL-2, CCL-3, and CCL-4. Examples of cytokines that may be stimulated by the cationic lipid complexes of the present invention are IL-2, IL-8, IL-12 and IFN-γ. The inventors contemplate that the cationic lipid complexes of the present invention may stimulate chemokines and cytokines in addition to those disclosed in this specification.

Lipids

The chiral cationic lipid complexes of the present invention may form liposomes that are optionally mixed with antigen and may contain the chiral cationic lipids alone or chiral cationic lipids in combination with neutral lipids. Suitable chiral cationic lipid species include, but are not limited to the R and S enantiomers of 3-β[$^4$N—($^1$N,$^8$-diguanidino spermidine)-carbamoyl]cholesterol (BGSC); 3-β[N,N-diguanidinoethyl-aminoethane)-carbamoyl]cholesterol (BGTC); N,N$^1$N$^2$N$^3$Tetra-methyltetrapalmitylspermine (cellfectin); N-t-butyl-N'-tetradecyl-3-tetradecyl-aminopropion-amidine (CLONfectin); dimethyldioctadecyl ammonium bromide (DDAB); 1,2-dimyristyloxypropyl-3-dimethyl-hydroxy ethyl ammonium bromide (DMRIE); 2,3-dioleoyloxy-N-[2 (sperminecarboxamido) ethyl]-N,N-dimethyl-1-p-ropanaminium trifluorocetate) (DOSPA); 1,3-dioleoyloxy-2-(6-carboxyspermyl)-propyl amide (DOSPER); 4-(2,3-bis-palmitoyloxy-propyl)-1-methyl-1H-imidazole (DPIM) N,N,N',N'-tetramethyl-N,N'-bis(2-hydroxyethyl)-2,3dioleoyloxy-1,4-butanediammonium iodide) (Tfx-50); N-1-(2,3-dioleoyloxy) propyl-N,N,N-trimethyl ammonium chloride (DOTMA) or other N—(N,N-1-dialkoxy)-alkyl-N,N,N-trisubstituted ammonium surfactants; 1,2-dioleoyl-3-(4'-trimethylammonio) butanol-sn-glycerol (DOBT) or cholesteryl (4'trimethylammonia) butanoate (ChOTB) where the trimethylammonium group is connected via a butanol spacer arm to either the double chain (for DOTB) or cholesteryl group (for ChOTB); DORI (DL-1,2-dioleoyl-3-dimethylaminopropyl-β-hydroxyethylammonium) or DORIE (DL-1,2-O-dioleoyl-3-dimethylaminopropyl-(3-hydroxyethylammoniu-m) (DORIE) or analogs thereof as disclosed in WO 93/03709; 1,2-dioleoyl-3-succinyl-sn-glycerol choline ester (DOSC); cholesteryl hemisuccinate ester (ChOSC); lipopolyamines such as dioctadecylamidoglycylspermine (DOGS) and dipalmitoyl phosphatidylethanolamylspermine (DPPES) or the cationic lipids disclosed in U.S. Pat. No. 5,283,185, cholesteryl-3β-carboxyl-amido-ethylenetrimethylammonium iodide, 1-dimethylamino-3-trimethylammonio-DL-2-propyl-cholesteryl carboxylate iodide, cholesteryl-3-O-carboxyamidoethyleneamine, cholesteryl-3-β-oxysuccinamido-ethylenetrimethylammonium iodide, 1-dimethylamino-3-trimethylammonio-DL-2-propyl-cholesteryl-3-β-oxysuccinate iodide, 2-(2-trimethylammonio)-ethylmethylamino ethyl-cholesteryl-3-β-oxysuccinate iodide, 3-β-N—(N',N'-dimethylaminoethane) carbamoyl cholesterol (DC-chol), and 3-β-N-(polyethyleneimine)-carbamoylcholesterol; O,O'-dimyristyl-N-lysyl aspartate (DMKE); O,O'-dimyristyl-N-lysyl-glutamate (DMKD); 1,2-dimyristyloxypropyl-3-dimethyl-hydroxy ethyl ammonium bromide (DMRIE); 1,2-dilauroyl-sn-glycero-3-ethylphosphocholine (DLEPC); 1,2-dimyristoyl-sn-glycero-3-ethylphosphocholine (DMEPC); 1,2-dioleoyl-sn-glycero-3-ethylphosphocholine (DOEPC); 1,2-dipalmitoyl-sn-glycero-3-ethylphosphocholine (DPEPC); 1,2-distearoyl-sn-glycero-3-ethylphosphocholine (DSEPC); 1,2-dioleoyl-3-trimethylammoninum propane (DOTAP); dioleoyl dim ethylaminopropane (DODAP); 1,2-palmitoyl-3-trimethyl-ammonium propane (DPTAP); 1,2-distearoyl-3-trimethyl-ammonium propane (DSTAP), 1,2-myristoyl-3-trimethyl-ammonium propane (DMTAP); and sodium dodecyl sulfate (SDS). The present invention contemplates the use of structural variants and derivatives of the cationic lipids disclosed in this application.

Certain aspects of the present invention include nonsteroidal chiral cationic lipids having a structure represented by the following formula:

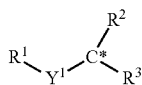

wherein in R' is a quaternary ammonium group, $Y^1$ is chosen from a hydrocarbon chain, an ester, a ketone, and a peptide, C* is a chiral carbon, $R^2$ and $R^3$ are independently chosen from a saturated fatty acid, an unsaturated fatty acid, an ester-linked hydrocarbon, phosphor-diesters, and combinations thereof. DOTAP, DMTAP, DSTAP, DPTAP, DPEPC, DSEPC, DMEPC, DLEPC, DOEPC, DMKE, DMKD, DOSPA, DOTMA, are examples of lipids having this general structure.

In one embodiment, chiral cationic lipids of the invention are lipids in which bonds between the lipophilic group and the amino group are stable in aqueous solution. Thus, an attribute of the complexes of the invention is their stability during storage (i.e., their ability to maintain a small diameter and retain biological activity over time following their formation). Such bonds used in the cationic lipids include amide bonds, ester bonds, ether bonds and carbamoyl bonds. Those of skill in the art would readily understand that liposomes containing more than one cationic lipid species may be used to produce the complexes of the present invention. For example, liposomes comprising two cationic lipid species, lysyl-phosphatidylethanolamine and β-alanyl cholesterol ester have been disclosed for certain drug delivery applications [Brunette, E. et al., Nucl. Acids Res., 20:1151 (1992)].

It is to be further understood that in considering chiral cationic liposomes suitable for use in the invention and optionally mixing with antigen, the methods of the invention are not restricted only to the use of the cationic lipids recited above but rather, any lipid composition may be used so long as a cationic liposome is produced and the resulting cationic charge density is sufficient to activate and induce an immune response.

Thus, the complexes of the invention may contain other lipids in addition to the chiral cationic lipids. These lipids include, but are not limited to, lyso lipids of which lyso-phosphatidylcholine (1-oleoyl lysophosphatidylcholine) is an example, cholesterol, or neutral phospholipids including dioleoyl phosphatidyl ethanolamine (DOPE) or dioleoyl phosphatidylcholine (DOPC) as well as various lipophilic surfactants, containing polyethylene glycol moieties, of which Tween-80 and PEG-PE are examples.

The chiral cationic lipid complexes of the invention may also contain negatively charged lipids as well as cationic lipids so long as the net charge of the complexes formed is positive and/or the surface of the complex is positively charged. Negatively charged lipids of the invention are those comprising at least one lipid species having a net negative charge at or near physiological pH or combinations of these. Suitable negatively charged lipid species include, but are not limited to, CREMS (cholesteryl hemisuccinate), NGPE (N-glutaryl phosphatidlylethanolanine), phosphatidyl glycerol and phosphatidic acid or a similar phospholipid analog.

Methods for producing the liposomes to be used in the production of the lipid comprising drug delivery complexes of the present invention are known to those of ordinary skill in the art. A review of methodologies of liposome preparation may be found in Liposome Technology (CFC Press New York 1984); Liposomes by Ostro (Marcel Dekker, 1987); Methods Biochem Anal, 33:337-462 (1988) and U.S. Pat. No. 5,283,185. Such methods include freeze-thaw extrusion and sonication. Both unilamellar liposomes (less than about 200 nm in average diameter) and multilamellar liposomes (greater than about 300 nm in average diameter) may be used as starting components to produce the complexes of this invention.

In the cationic liposomes utilized to produce the cationic lipid complexes of this invention, the chiral cationic lipid is present in the liposome at from about 10 mole % to about 100 mole % of total liposomal lipid, or from about 20 mole % to about 80 mole %. The neutral lipid, when included in the liposome, may be present at a concentration of from about 0 mole % to about 90 mole % of the total liposomal lipid, or from about 20 mole % to about 80 mole %, or from 40 mole % to 80 mole %. The negatively charged lipid, when included in the liposome, may be present at a concentration ranging from about 0 mole % to about 49 mole % of the total liposomal lipid, or from about 0 mole % to about 40 mole %. In one embodiment, the liposomes contain a chiral cationic and a neutral lipid, in ratios between about 2:8 to about 6:4.

It is further understood that the complexes of the present invention may contain modified lipids, protein, polycations or receptor ligands which function as a targeting factor directing the complex to a particular tissue or cell type. Examples of targeting factors include, but are not limited to, asialoglycoprotein, insulin, low density lipoprotein (LDL), folate and monoclonal and polyclonal antibodies directed against cell surface molecules. Furthermore, to modify the circulatory half-life of the complexes, the positive surface charge can be sterically shielded by incorporating lipophilic surfactants which contain polyethylene glycol moieties.

The cationic lipid complexes may be stored in isotonic sucrose or dextrose solution upon collection from the sucrose gradient or they may be lyophilized and then reconstituted in an isotonic solution prior to use. In one embodiment, the cationic lipid complexes are stored in solution. The stability of the cationic lipid complexes of the present invention is measured by specific assays to determine the physical stability and biological activity of the cationic lipid complexes over time in storage. The physical stability of the cationic lipid complexes is measured by determining the diameter and charge of the cationic lipid complexes by methods known to those of ordinary skill in the art, including for example, electron microscopy, gel filtration chromatography or by means of quasi-elastic light scattering using, for example, a Coulter N4SD particle size analyzer as described in the Example. The physical stability of the cationic lipid complex is "substantially unchanged" over storage when the diameter of the stored cationic lipid complexes is not increased by more than 100%, or by not more than 50%, or by not more than 30%, over the diameter of the cationic lipid complexes as determined at the time the cationic lipid complexes were purified.

While it is possible for the chiral cationic lipid to be administered in a pure or substantially pure form, it is preferable to present it as a pharmaceutical composition, formulation or preparation. Pharmaceutical formulations using the chiral cationic lipid complexes of the invention may comprise the cationic lipid complexes in a physiologically compatible sterile buffer such as, for example, phosphate buffered saline, isotonic saline or low ionic strength buffer such as acetate or Hepes (an exemplary pH being in the range of about 3.0 to about 8.0). The chiral cationic lipid complexes may be administered as aerosols or as liquid solutions for intratumoral, intraarterial, intravenous, intratracheal, intraperitoneal, subcutaneous, and intramuscular administration.

The formulations of the present invention may incorporate any stabilizer known in the art. Illustrative stabilizers are cholesterol and other sterols that may help rigidify the liposome bilayer and prevent disintegration or destabilization of the bilayer. Also agents such as polyethylene glycol, poly-, and monosaccharides may be incorporated into the liposome to modify the liposome surface and prevent it from being destabilized due to interaction with blood-components. Other illustrative stabilizers are proteins, saccharides, inorganic acids, or organic acids which may be used either on their own or as admixtures.

A number of pharmaceutical methods may be employed to control, modify, or prolong the duration of immune stimulation. Controlled release preparations may be achieved through the use of polymer complexes such as polyesters, polyamino acids, methylcellulose, polyvinyl, poly(lactic acid), and hydrogels to encapsulate or entrap the cationic lipids and slowly release them. Similar polymers may also be used to adsorb the liposomes. The liposomes may be contained in emulsion formulations in order to alter the release profile of the stimulant. Alternatively, the duration of the stimulant's presence in the blood circulation may be enhanced by coating the surface of the liposome with compounds such as polyethylene glycol or other polymers and other substances such as saccharides which are capable of enhancing the circulation time or half life of liposomes and emulsions.

When oral preparations are required, the chiral cationic lipids may be combined with typical pharmaceutical carriers known in the art such as, for example, sucrose, lactose, methylcellulose, carboxymethyl cellulose, or gum Arabic, among others. The cationic lipids may also be encapsulated in capsules or tablets for systemic delivery.

Administration of the chiral cationic lipid of the present invention may be for either a prophylactic or therapeutic purpose. When provided prophylactically, the cationic lipid is provided in advance of any evidence or symptoms of illness. When provided therapeutically, the cationic lipid is provided at or after the onset of disease. The therapeutic administration of the immune-stimulant serves to attenuate or cure the disease. For both purposes, the cationic lipid may be administered with an additional therapeutic agent(s) or antigen(s). When the cationic lipids are administered with an additional therapeutic agent or antigen, the prophylactic or therapeutic effect may be generated against a specific disease.

The formulations of the present invention, both for veterinary and for human use, comprise a chiral cationic lipid alone as described above, as a mixture of R and S enantiomers, or also optionally, with one or more therapeutic ingredients such as an antigen(s) or drug molecule(s). The formulations may conveniently be presented in unit dosage form and may be prepared by any method known in the pharmaceutical art.

Antigens

In one embodiment, the chiral cationic lipid is administered without any additional agents in order to boost or lower various immune responses, including production of other immune modulators, and to boost the immune response to fighting disease. In another embodiment, the chiral cationic lipid is administered in combination with an antigen or antigens. In this case the objective is to generate an immune response, which is specific to the antigen(s) delivered in combination with the cationic lipid. The response generated may include production of specific cytotoxic T-cells, memory T-cells, or B-cells resulting in the prevention of or therapeutic response to the specific disease associated with those antigen(s). The antigen can be any tumor-associated antigen or microbial antigen or any other antigen known to one skilled in the art.

A "tumor-associated antigen," as used herein is a molecule or compound (e.g., a protein, peptide, polypeptide, lipoprotein, lipopeptide, glycoprotein, glycopeptides, glycolipid, carbohydrate, RNA, and/or DNA) associated with a tumor or cancer cell and which is capable of provoking an immune response (humoral and/or cellular) when expressed on the surface of an antigen presenting cell in the context of a major histocompatibility complex ("MHC") molecule. Tumor-associated antigens include self antigens, as well as other antigens that may not be specifically associated with a cancer, but nonetheless enhance an immune response to and/or reduce the growth of a tumor or cancer cell when administered to an animal. More specific embodiments are provided herein.

A "microbial antigen," as used herein, is an antigen of a microorganism and includes, but is not limited to, infectious virus, infectious bacteria, infectious parasites and infectious fungi. Microbial antigens may be intact microorganisms, and natural isolates, fragments, or derivatives thereof, synthetic compounds which are identical to or similar to naturally-occurring microbial antigens and, preferably, induce an immune response specific for the corresponding microorganism (from which the naturally-occurring microbial antigen originated). In a preferred embodiment, a compound is similar to a naturally-occurring microorganism antigen if it induces an immune response (humoral and/or cellular) similar to a naturally-occurring microorganism antigen. Compounds or antigens that are similar to a naturally-occurring microorganism antigen are well known to those of ordinary skill in the art such as, for example, a protein, peptide, polypeptide, lipoprotein, lipopeptide, glycoprotein, glycopeptides, lipid, glycolipid, carbohydrate, RNA, and/or DNA. Another nonlimiting example of a compound that is similar to a naturally-occurring microorganism antigen is a peptide mimic of a polysaccharide antigen. More specific embodiments are provided herein.

The term "antigen" is further intended to encompass peptide or protein analogs of known or wild-type antigens such as those described in this specification. The analogs may be more soluble or more stable than wild type antigen, and may also contain mutations or modifications rendering the antigen more immunologically active. Antigen can be modified in any manner, such as adding lipid or sugar moieties, mutating peptide or protein amino acid sequences, mutating the DNA or RNA sequence, or any other modification known to one skilled in the art. Antigens can be modified using standard methods known by one skilled in the art.

Also useful in the compositions and methods of the present invention are peptides or proteins which have amino acid sequences homologous with a desired antigen's amino acid sequence, where the homologous antigen induces an immune response to the respective tumor, microorganism or infected cell.

In one embodiment, the antigen in the cationic lipid complex comprises an antigen associated with a tumor or cancer, i.e., a tumor-associated antigen, to make a vaccine to prevent or treat a tumor. As such, in one embodiment, the tumor or cancer vaccines of the present invention further comprise at least one epitope of at least one tumor-associated antigen. In another preferred embodiment, the tumor or cancer vaccines of the present invention further comprise a plurality of epitopes from one or more tumor-associated antigens. The tumor-associated antigens finding use in the cationic lipid complexes and methods of the present invention can be inherently immunogenic, or nonimmunogenic, or slightly immunogenic. As demonstrated herein, even tumor-associated self antigens may be advantageously employed in the subject vaccines for therapeutic effect, since the subject compositions are capable of breaking immune tolerance against such antigens. Exemplary antigens include, but are not limited to, synthetic, recombinant, foreign, or homologous antigens, and antigenic materials may include but are not limited to proteins, peptides, polypeptides, lipoproteins, lipopeptides, lipids, glycolipids, carbohydrates, RNA and DNA. Examples of such vaccines include, but are not limited to, those for the treatment or prevention of breast cancer, head and neck cancer, melanoma, cervical cancer, lung cancer, prostate cancer, gut carcinoma, or any other cancer known in the art using a cationic lipid in a complex with a tumor-associated antigen(s). It is also possible to formulate the antigen with the cationic lipid without encapsulating it in the liposome. Thus, the chiral cationic lipid complexes of the present invention may be used in methods to treat or prevent cancer. In such a case, the mammal to be immunized may be injected with the pharmaceutical formulation containing the liposome with the encapsulated antigen(s).

Tumor-associated antigens suitable for use in the present invention include both naturally occurring and modified molecules which may be indicative of single tumor type, shared among several types of tumors, and/or exclusively expressed or overexpressed in tumor cells in comparison with normal cells. In addition to proteins, glycoproteins, lipoproteins, peptides, and lipopeptides, tumor-specific patterns of expression of carbohydrates, gangliosides, glycolipids, and mucins have also been documented. Exemplary tumor-associated antigens for use in cancer vaccines include protein products of oncogenes, tumor suppressor genes, and other genes with mutations or rearrangements unique to tumor cells, reactivated embryonic gene products, oncofetal antigens, tissue-specific (but not tumor-specific) differentiation antigens, growth factor receptors, cell surface carbohydrate residues, foreign viral proteins, and a number of other self proteins.

Specific embodiments of tumor-associated antigens include, e.g., mutated or modified antigens such as the protein products of the Ras p21 protooncogenes, tumor suppressor p53 and HER-2/neu and BCR-abl oncogenes, as well as CDK4, MUM1, Caspase 8, and Beta catenin; over-expressed antigens such as galectin 4, galectin 9, carbonic anhydrase, Aldolase A, PRAME, Her2/neu, ErbB-2 and KSA, oncofetal antigens such as alpha fetoprotein (AFP), human chorionic gonadotropin (hCG); self antigens such as carcinoembryonic antigen (CEA) and melanocyte differentiation antigens such as Mart 1/Melan A, gp100, gp75, Tyrosinase, TRP1 and TRP2; prostate associated antigens such as PSA, PAP, PSMA, PSM-P1 and PSM-P2; reactivated embryonic gene products such as MAGE 1, MAGE 3, MAGE 4, GAGE 1, GAGE 2, BAGE, RAGE, and other cancer testis antigens such as NY-ESO1, SSX2 and SCP1; mucins such as Muc-1 and Muc-2; gangliosides such as GM2, GD2 and GD3, neutral glycolipids and glycoproteins such as Lewis (y) and globo-H; and glycoproteins such as Tn, Thompson-Freidenreich antigen (TF) and sTn. Also included as tumor-associated antigens herein are whole cell and tumor cell lysates as well as immunogenic portions thereof, as well as immunoglobulin idiotypes expressed on monoclonal proliferations of B lymphocytes for use against B cell lymphomas.

Tumor-associated antigens and their respective tumor cell targets include, e.g., cytokeratins, particularly cytokeratin 8, 18 and 19, as antigens for carcinoma. Epithelial membrane antigen (EMA), human embryonic antigen (HEA-125), human milk fat globules, MBr1, MBr8, Ber-EP4, 17-1A, C26 and T16 are also known carcinoma antigens. Desmin and muscle-specific actin are antigens of myogenic sarcomas. Placental alkaline phosphatase, beta-human chorionic gonadotropin, and alpha-fetoprotein are antigens of trophoblastic and germ cell tumors. Prostate specific antigen is an antigen of prostatic carcinomas, carcinoembryonic antigen of colon adenocarcinomas. HMB-45 is an antigen of melanomas. In cervical cancer, useful antigens could be encoded by human papilloma virus. Chromagranin-A and synaptophysin are antigens of neuroendocrine and neuroectodermal tumors. Of particular interest are aggressive tumors that form solid tumor masses having necrotic areas. The lysis of such necrotic cells is a rich source of antigens for antigen-presenting cells, and thus the subject therapy may find advantageous use in conjunction with conventional chemotherapy and/or radiation therapy.

In one embodiment, the human papillomavirus HPV antigens are used. A specific HPV antigen that used as a tumor-associated antigen is HPV subtype 16 E7. HPV E7 antigen-cationic lipid complexes are effective at preventing and treating cervical cancer. In addition, a genetically engineered E7 protein, i.e., Elm protein, having antigenic activity, but without tumorigenic activity, is an effective tumor-associated antigen. Elm-cationic lipid complexes induce cellular immunity to cause complete regression of established tumors and, thus, are useful as potent anti-cervical cancer vaccines.

Tumor-associated antigens can be prepared by methods well known in the art. For example, these antigens can be prepared from cancer cells either by preparing crude extracts of cancer cells (e.g., as described in Cohen et al., Cancer Res., 54:1055 (1994)), by partially purifying the antigens, by recombinant technology, or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

Antigens derived from pathogens known to predispose to certain cancers may also be advantageously included in the cancer vaccines of the present invention. It is estimated that close to 16% of the worldwide incidence of cancer can be attributed to infectious pathogens; and a number of common malignancies are characterized by the expression of specific viral gene products. Thus, the inclusion of one or more antigens from pathogens implicated in causing cancer may help broaden the host immune response and enhance the prophylactic or therapeutic effect of the cancer vaccine. Pathogens of particular interest for use in the cancer vaccines provided herein include the, hepatitis B virus (hepatocellular carcinoma), hepatitis C virus (heptomas), Epstein Barr virus (EBV) (Burkitt lymphoma, nasopharynx cancer, PTLD in immunosuppressed individuals), HTLVL (adult T cell leukemia), oncogenic human papilloma viruses types 16, 18, 33, 45 (adult cervical cancer), and the bacterium *Helicobacter pylori* (B cell gastric lymphoma). Other medically relevant microorganisms that may serve as antigens in mammals and more particularly humans are described extensively in the literature, e.g., C. G. A Thomas, Medical Microbiology, Bailliere Tindall, Great Britain 1983, the entire contents of which is hereby incorporated by reference.

In another embodiment, the antigen in the cationic lipid complex comprises an antigen derived from or associated with a pathogen, i.e., a microbial antigen. As such, in one embodiment, the pathogen vaccines of the present invention further comprise at least one epitope of at least one microbial antigen. Pathogens that may be targeted by the subject vaccines include, but are not limited to, viruses, bacteria, parasites and fungi. In another embodiment, the pathogen vaccines of the present invention further comprise a plurality of epitopes from one or more microbial antigens.

The microbial antigens finding use in the cationic lipid complexes and methods may be inherently immunogenic, or nonimmunogenic, or slightly immunogenic. Exemplary antigens include, but are not limited to, synthetic, recombinant, foreign, or homologous antigens, and antigenic materials may include but are not limited to proteins, peptides, polypeptides, lipoproteins, lipopeptides, lipids, glycolipids, carbohydrates, RNA, and DNA.

Exemplary viral pathogens include, but are not limited to, viruses that infect mammals, and more particularly humans. Examples of virus include, but are not limited to: Retroviridae (e.g., human immunodeficiency viruses), such as HIV-1 (also referred to as HTLV-III, LAV or HTLV-III/LAV, or HIV-III; and other isolates, such as HIV-LP; Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Coronaviridae (e.g. coronaviruses); Rhabdoviridae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bungaviridae (e.g. Hantaan viruses, bunga viruses, phleboviruses and Nairo viruses); Arena viridae (hemorrhagic fever viruses); Reoviridae (e.g. reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

Also, gram negative and grain positive bacteria may be targeted by the subject compositions and methods in vertebrate animals. Such grain positive bacteria include, but are not limited to *Pasteurella* species, Staphylococci species, and *Streptococcus* species. Gram negative bacteria include, but are not limited to, *Escherichia coli, Pseudomonas* species, and *Salmonella* species. Specific examples of infectious bacteria include but are not limited to: *Helicobacter pyloris, Borella burgdorferi, Legionella pneumophilia, Mycobacteria* sps (e.g. *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus infuenzae, Bacillus antracis, corynebacterium diphtherias, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nucleation, Streptobacillus moniliformis,*

*Treponema pallidium, Treponema pertenue, Leptospira, Rickettsia,* and *Actinomyces israelli.*

Polypeptides of bacterial pathogens which may find use as sources of microbial antigens in the subject compositions include but are not limited to an iron-regulated outer membrane protein, ("IROMP"), an outer membrane protein ("OMP"), and an A-protein of *Aeromonis salmonicida* which causes furunculosis, p57 protein of *Renibacterium salmoninarum* which causes bacterial kidney disease ("BKD"), major surface associated antigen ("msa"), a surface expressed cytotoxin ("mpr"), a surface expressed hemolysin ("ish"), and a flagellar antigen of *Yersiniosis*; an extracellular protein ("ECP"), an iron-regulated outer membrane protein ("TROMP"), and a structural protein of *Pasteurellosis*; an OMP and a flagellar protein of *Vibrosis anguillarum* and *V. ordalii*; a flagellar protein, an OMP protein, aroA, and purA of *Edwardsiellosis ictaluri* and *E. tarda*; and surface antigen of *Ichthyophthirius*; and a structural and regulatory protein of *Cytophaga columnari*; and a structural and regulatory protein of *Rickettsia*. Such antigens can be isolated or prepared recombinantly or by any other means known in the art.

Examples of pathogens further include, but are not limited to, fungi that infect mammals, and more particularly humans. Examples of fungi include, but are not limited to: *Cryptococcus neoformans, Histoplasma capsulatum, Coccidioides immitis, Blastomyces dermatitidis, Chlamydia trachomatis,* and *Candida albicans*. Examples of infectious parasites include *Plasmodium* such as *Plasmodium falciparum, Plasmodium malariae, Plasmodium ovale,* and *Plasmodium vivax*. Other infectious organisms (i.e. protists) include *Toxoplasma gondii*. Polypeptides of a parasitic pathogen include but are not limited to the surface antigens of *Ichthyophthirius*.

Other medically relevant microorganisms that serve as antigens in mammals and more particularly humans are described extensively in the literature (e.g., see C. G. A Thomas, Medical Microbiology, Bailliere Tindall, Great Britain 1983). In addition to the treatment of infectious human diseases and human pathogens, the compositions and methods of the present invention are useful for treating infections of nonhuman mammals. Many vaccines for the treatment of nonhuman mammals are disclosed in Bennett, K. Compendium of Veterinary Products, 3rd ed. North American Compendiums, Inc., 1995; see also WO 02/069369, the disclosure of which is expressly incorporated by reference herein in its entirety.

Exemplary nonhuman pathogens include, but are not limited to, mouse mammary tumor virus ("MMTV"), Rous sarcoma virus ("RSV"), avian leukemia virus ("ALV"), avian myeloblastosis virus ("AMV"), murine leukemia virus ("MLV"), feline leukemia virus ("FeLV"), murine sarcoma virus ("MSV"), gibbon ape leukemia virus ("GALV"), spleen necrosis virus ("SNV"), reticuloendotheliosis virus ("RV"), simian sarcoma virus ("SSV"), Mason-Pfizer monkey virus ("MPMV"), simian retrovirus type 1 ("SRV-1"), lentiviruses such as HIV-1, HIV-2, SIV, Visna virus, feline immunodeficiency virus ("FIV"), and equine infectious anemia virus ("EIAV"), T-cell leukemia viruses such as HTLV-1, HTLV-II, simian T-cell leukemia virus ("STLV"), and bovine leukemia virus ("BLV"), and foamy viruses such as human foamy virus ("HFV"), simian foamy virus ("SFV") and bovine foamy virus ("BFV").

In some embodiments, "treatment," "treat," and "treating," as used herein with reference to infectious pathogens, refer to a prophylactic treatment which increases the resistance of a subject to infection with a pathogen or decreases the likelihood that the subject will become infected with the pathogen; and/or treatment after the subject has become infected in order to fight the infection, e.g., reduce or eliminate the infection or prevent it from becoming worse.

Microbial antigens can be prepared by methods well known in the art. For example, these antigens can be prepared directly from viral and bacterial cells either by preparing crude extracts, by partially purifying the antigens, or alternatively by recombinant technology or by de novo synthesis of known antigens. The antigen may also be in the form of a nucleic acid encoding an antigenic peptide in a form suitable for expression in a subject and presentation to the immune system of the immunized subject. Further, the antigen may be a complete antigen, or it may be a fragment of a complete antigen comprising at least one epitope.

In order to improve incorporation of the antigen into the chiral cationic lipid vesicles and also to improve delivery to the cells of the immune system, the antigen may be conjugated to a lipid chain in order to improve its solubility in the hydrophobic acyl chains of the cationic lipid, while maintaining the antigenic properties of the molecule. The lipidated antigen can be a lipoprotein, or a lipopeptide, and combinations thereof. The lipidated antigen may have a linker conjugated between the lipid and the antigen such as, for example, an N-terminal α or ε-palmitoyl lysine may be connected to antigen via a dipeptide Ser-Ser linker. U.S. application Ser. No. 12/049,957 discloses that the DOTAP/E7-lipopeptide complex exhibited an enhanced functional antigen-specific $CD8^+$ T lymphocyte responses in vivo compared to the DOTAP/E7 formulation, and therefore provided superior anti-tumor efficacy.

The present invention will be further appreciated in light of the following example.

Example

Effective Stimulation of the Immune System by Enantiomers of Cationic Lipids

1. Cell Lines and Peptides

TC-1 cells are C57BL/6 mouse lung endothelial cells that have been transformed with the HPV16 E6 and E7 oncogenes and activated H-ras. Cells were grown in RPMI medium (commercially available from Invitrogen of Carlsbad, Calif.) supplemented with 10% fetal bovine serum and 100 U/ml penicillin, and 100 mg/ml streptomycin. The MHC class I restricted peptide from the HPV 16 E7 protein (amino acid 11 to 20, YMLDLQPETT [SEQ. ID. NO. 1]) was synthesized by the University of Pittsburgh Peptide Synthesis Facility by solid state synthesis using an Advanced ChemTech model 200 peptide synthesizer and purified by HPLC.

2. Preparation of Lipid/Antigen Complexes and Determination of Physical Properties The enantiomers of DOTAP were supplied by Merck AG (EPROVA), Switzerland. All other lipids were purchased from Avanti Polar Lipids (Alabaster, Ala.). Small unilamellar DOTAP liposomes were prepared by thin film hydration followed by extrusion. The lipid, in chloroform, was dried as a thin layer under a stream of nitrogen in a glass tube. The thin film was vacuum desiccated for 2-3 h and then re-hydrated in cell culture grade water (commercially available from Cambrex of Walkersville, Md.) or buffer (such buffers are well known to those skilled in the art) containing E7 peptide to a final concentration of 0.7 mg lipids and 0.1 mg E7 per mL (molar ratio=11:1). The lipid dispersion was sequentially extruded through polycarbonate membranes with pore size of 0.4, 0.2, and 0.1 µm. The un-entrapped peptide was not removed. The liposomes were stored at 4° C. until use. E7 peptide association with the liposome was determined by measuring the percentage of liposome-bound peptide. In brief, unbound E7 peptide from R-DOTAP/E7, S-DOTAP/E7 or RS-DOTAP/E7 complexes was separated by a Microcon® centrifugal filtrate device (Millipore, Bedford, Mass.) and the concentration of unbound peptide was measured by Micro BCA™ Protein Assay Kit (Pierce, Rockford, Ill.). The efficiency of peptide association was determined as percent unbound peptide. Other methods used in general liposome preparation that are well known to those skilled in the art may also be used.

3. Statistical Analysis

Data are presented as mean±SD of at least 3 independent experiments. Two-tailed Student's t tests were used to assess statistical significance for differences in means. Significance was set at $p<0.05$.

4. Individual R and S Enantiomers of Cationic Lipid/E7 Complexes Activate Human Dendritic Cells Similarly to the DOATP Racemic Mixture.

Cationic liposomes were prepared as described above. The E7 antigen used in the formulation is the identified human E7 peptide restricted by HLA-A*0201 [HPV-16 E7, amino acids 11-20, YMLDLQPETT (SEQ. ID. NO. 1)]. The peptide was synthesized by the University of Pittsburgh, Molecular Medicine Institute, Pittsburgh, Pa. Human HLA-A2 human dendritic cells were obtained from Lonza (of Walkersville, Md.). Frozen cryovials were thawed and the dendritic cells were cultured in LGM-3 medium (commercially available from Lonza of Walkersville, Md.) supplemented with 50 microgram/ml. IL-4 and GM-CSF at 37° C. and 5% $CO_2$ at an initial plating density of 125,000 cells/cm$^2$ in 2 nil of medium in 12-well tissue culture dishes. The cells were grown for 3 days in culture and appeared as a mixture of adherent and rounded cells by microscopic examination.

The cells were treated on day 3 with a fresh dose of 50 microgram/ml of IL-4 and GM-CSF (all wells) and test wells were treated with, either a mixture of interleukin 1-beta ("IL-β"), interleukin 6 ("IL-6") and TNF-α, at 10 ng/ml, and prostaglandin E2 ("PGE-2") at 10 µg/ml (positive control for activation), no treatment (negative activation control), and S-DOTAP/E7 at 2.5, 10 and 40 micromolar final concentrations, and R-DOTAP/E7 at 2.5, 10 and 40 micromolar final concentrations. The treated dendritic cells were maintained in culture for 24 hours and harvested for cell surface marker staining and flow cytometry analysis. The harvested cells were counted by hemacytometer and 10 µl of the following antibody conjugates were added sequentially to each sample for labeling surface markers: CD80-FITC, CD83-APC, and CD86-PE (BD Biosciences). The surface labeled cells were subsequently analyzed by flow cytometry using a BD FACxcaliber flow cytometer, and the co-stimulatory dendritic cell marker molecules CD80, CD83, and CD86 which are produced upon activation, were monitored. As seen in FIGS. 2, 3 and 4 primary human dendritic cells treated with the both enantiomers of the cationic lipid/E7 complex up-regulated the expression of all three co-stimulatory markers of dendritic cell activation evaluated and required for successful antigen presentation to T-cells, similarly to what was observed with the racemic mixture (RS-DOTAP) of the cationic lipid and reported in U.S. application Ser. No. 12/049,957, assigned to the assignee of the present application.

5. Cationic Lipid/E7 Complexes Consisting of Individual R and S Enantiomers Exhibit Different Potencies in Activating Human Dendritic Cells to Induce Chemokine and Cytokine Production Human HLA-A2 dendritic cells (Lonza, Walkersville, Md.), were treated and grown in culture as described above. On day 3 the cells were treated with 40 micromolar DOTAP/E7 complex or the potent immunostimulator lipopolysaccharide (LPS) at 50 micromolar concentrations (positive control). Medium from assay wells was removed and centrifuged at 1300 rpm in a microfuge for 5 minutes to pellet unattached dendritic cells. The supernatants were removed and treated with 10 microliters per ml of Calbiochem (La Jolla, Calif.) protease inhibitor cocktail set I (Cat. No. 539131) and stored frozen prior to analysis. Samples were analyzed for chemokine and cytokine expression by Searchlight Protein Array Multiplex ELISA assay [Pierce Biotechnology (Woburn, Mass.)].

Production of selected chemokines known to be essential in the cellular immune response, CCL3, CCL4, CCL5, and CCL19 was evaluated, and production of IL-2, IL-8 and IL-12 was evaluated (FIGS. 5-11, which illustrate the ability of R-DOTAP/E7 and S-DOTAP/E7 to induce production of CCL3, CCL4, CCL5, CCL-19, IL-2, IL-8 and IL-12). The figures illustrate that the DOTAP/E7 complex containing the individual enantiomers of DOTAP induce cytokine and chemokine production by human dendritic cells. Both enantiomers however activate the immune system to different extents with the R-enantiomer exhibiting higher potency.

6. Kinetics of TC-1 HPV-Positive Tumor Growth in Mice Treated with DOTAP/E7 Compositions at Varying Doses of Racemic Mixtures of DOTAP.

Figure 12:
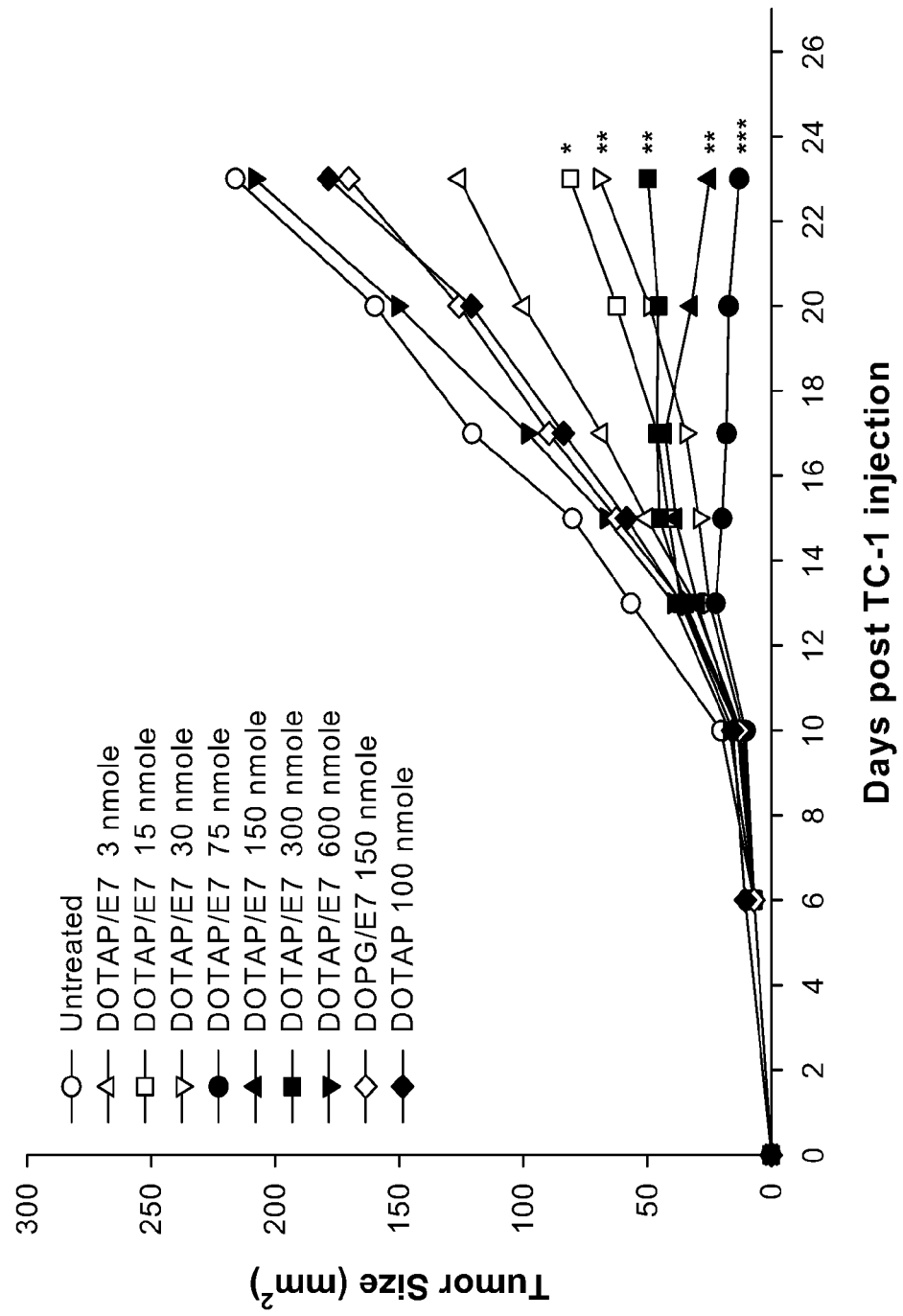
FIG. 12 is a graph demonstrating the in vivo antitumor effect of various doses of a cationic lipid/antigen complex based on tumor size and time post-injection.

In FIG. 12, mice were subcutaneously injected with TC-1 cells on day 0 in order to induce the growth of HPV-positive tumors. The DOTAP/E7 compositions were comprised of racemic mixtures of DOTAP. The mice received DOTAP/E7 compositions containing 10 µg E7 peptide subcutaneously on the opposite side of the abdomen on day 6. DOTAP lipid concentration in the complex varied from 3 to 600 mole (3, 15, 30, 75, 150, 300, and 600 nmole). Low dose of DOTAP (15 nmole) showed partial tumor inhibition effect (P<0.05) compared to the untreated control on day 23, while DOTAP at 30, 150 or 300 mmole exhibited an enhanced efficacy (P<0.01). DOTAP at 75 mmole showed the most significant tumor regression effect (P<0.001). Again, mice given a high dose of DOTAP (600 nmole) did not show anti-tumor activity, confirming that DOTAP liposomes at a high dose might have induced a negative regulation to the immune response. In addition, DOTAP liposomes at the 100 mmole dose, but without E7 peptide, did not show significant inhibition of tumor growth, indicating that the anti-tumor effect was antigen specific. Further, liposomes of 1,2-dioleoyl-sn-glycero-3-phosphoglycerol (DOPG), an anionic lipid, administered at the 150 nmole dose with antigen failed to significantly inhibit tumor growth.

7. Kinetics of TC-1 HPV-Positive Tumor Growth in Mice Treated with R-DOTAP/E7 and S-DOTAP Compositions at Varying Doses of R and S DOTAP.

Figure 13:
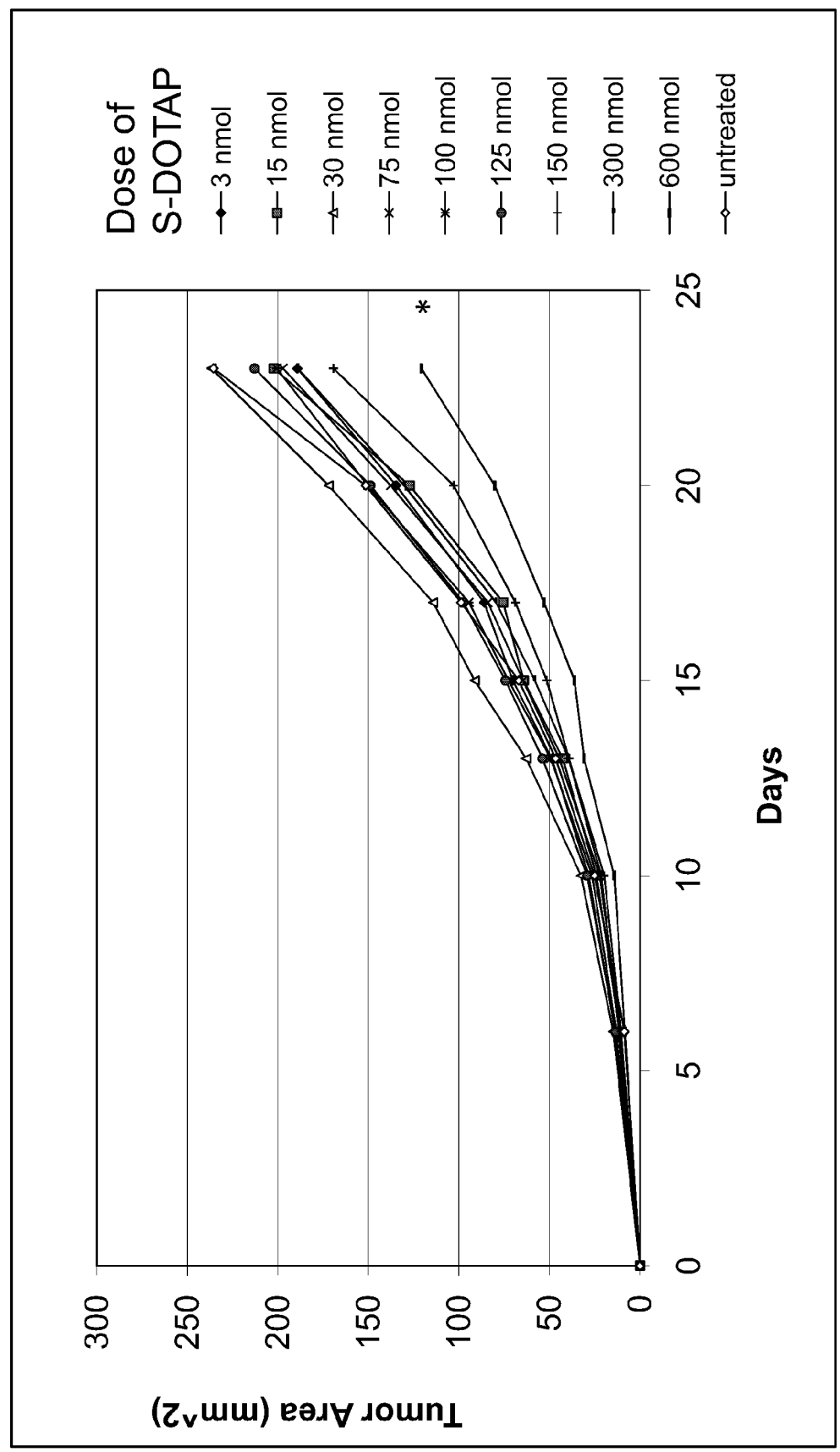
FIG. 13 is a graph demonstrating the effect of S-DOTAP dose on the in vivo anti tumor efficacy of the cationic lipid/antigen complex.
Figure 14:
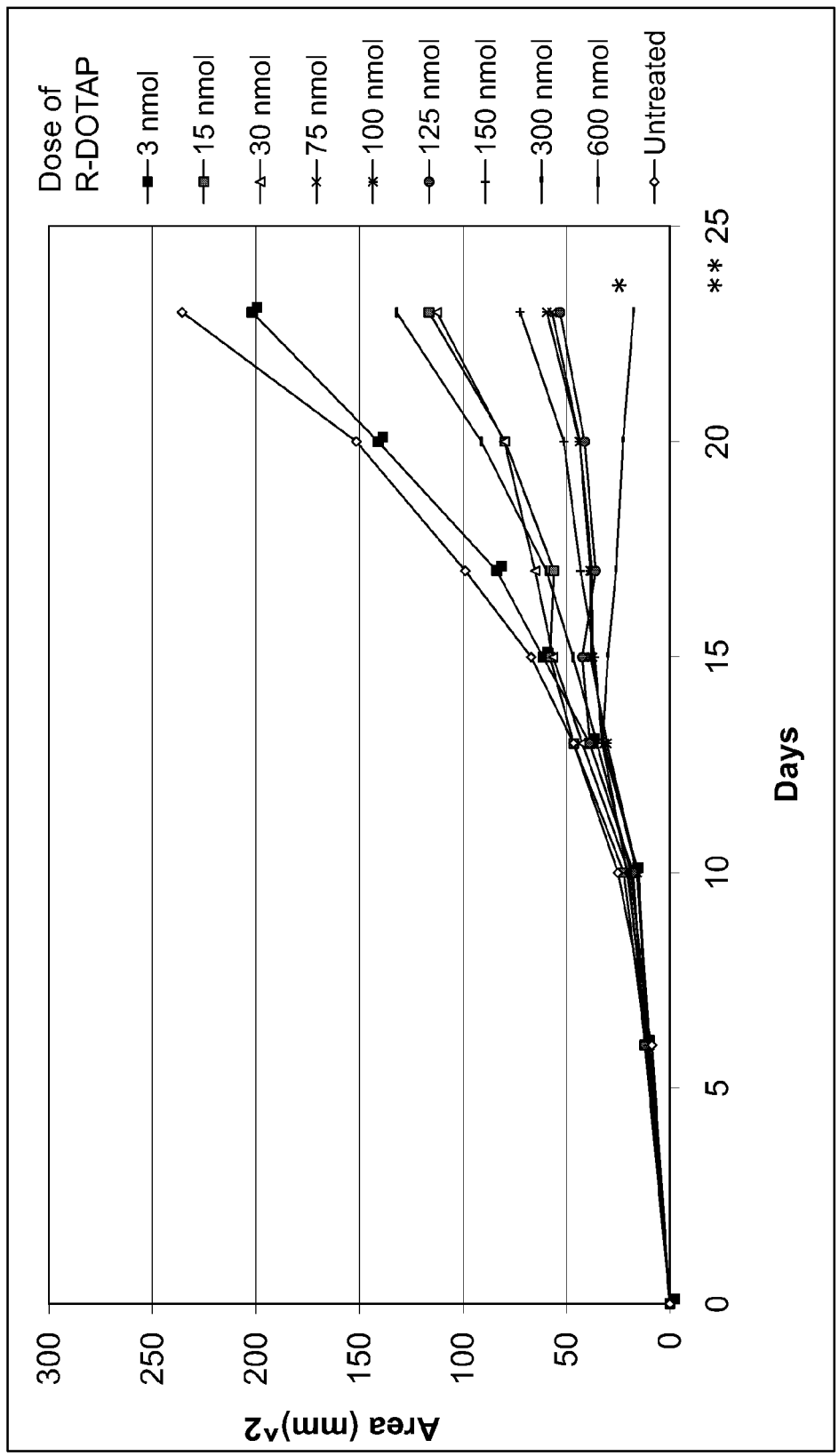
FIG. 14 is a graph demonstrating the effect of R-DOTAP dose on the in vivo anti tumor efficacy of the cationic lipid/antigen complex.

In FIGS. 13 and 14, mice were subcutaneously injected with TC-1 cells on day 0 in order to induce the growth of HPV-positive tumors. The mice received R and S-DOTAP/E7 compositions containing 20 μg E7 peptide subcutaneously on the opposite side of the abdomen on day 6. R or S-DOTAP lipid concentrations in the complex varied from 3 to 600 nmole (3, 15, 30, 75, 100, 125, 150, 300, and 600 nmole). Unlike the racemic mixture of DOTAP (FIG. 12), S-DOTAP complexes did not exhibit the ability to inhibit tumor growth and no tumor regression was observed (FIG. 13). A dose response effect was however observed, and S-DOTAP doses of 600 nmole induced the slowest tumor growth ($P<0.05$) compared to untreated control on day 23. Referring to FIG. 14 the anti-tumor effect of complexes containing R-DOTAP and antigen were similar to the effect observed in the racemic mixture (FIG. 12). 75-150 nmole doses of R-DOTAP showed partial tumor inhibition effect ($P<0.001$) compared to the untreated control on day 23, while R-DOTAP at 300 nmole exhibited the most significant tumor regression efficacy ($P<0.0001$). Again, mice given a high dose of R-DOTAP (600 mole) did not show significant anti-tumor activity, confirming that R-DOTAP liposomes at a high dose might have induced a negative regulation to the immune response. E7 peptide alone, did not show any inhibition of tumor growth (not shown). FIG. 15 shows the lipid dose-response curves for the tumor regression efficacy of the various cationic lipid/E7 antigen complexes DOTAP, S-DOTAP, and R-DOTAP at 20 μg of the antigen and DOTAP at 10 μg of the antigen.

8. Induction of T Cell Proliferation by S-DOTAP and R-DOTAP Compositions.

We have previously demonstrated that in U.S. Provisional Application No. 60/983,799, assigned to the assignee of the present application, that DOTAP/E7 interacts directly with human T lymphocytes, leading to clonal expansion and T cell activation. Those studies examined the ability of racemic mixtures of DOTAP to stimulate clonal expansion of T cells. In those studies, enriched human lymphocytes obtained from an HLA-A2$^+$ healthy donor were directly stimulated by medium, DOTAP alone, peptide alone or DOTAP/hE7. The stimulation was repeated three times with a 7-day interval. Three days after the third stimulation, lymphocytes treated with DOTAP or DOTAP/E7 showed extensive expansion of T cell colonies in culture in contrast to no clonal expansion in medium control. The expanded T-cells also demonstrated significant CTL activity.

In those studies, the DOTAP-mediated T cell activation was further confirmed by ERK phosphorylation in T cells. DOTAP-induced expression of the costimulatory molecule, CD86 on human T lymphocytes was also observed. Those results suggested that DOTAP has a direct impact on T cell activation via a MAP kinase mediated cell proliferation.

In the present studies, the induction of human T-cell proliferation by the R and S enantiomers of DOTAP was investigated and confirmed using purified T-cells obtained from Lonza, Mass. R-DOTAP induced more T-cell proliferation than S-DOTAP and was similar in activity to the DOTAP racemic mixture.

Discussion

As described in U.S. Pat. No. 7,303,881, a broad class of cationic lipids can act as potent immunostimulators together with an antigen to generate antigen specific immune responses in the treatment of disease. For example, U.S. Pat. No. 7,303,881 discloses that liposomes comprised of cationic lipids activate dendritic cells as demonstrated by the stimulation by cationic lipids of the expression of costimulatory molecules CD80/CD86 on DC2.4 dendritic cells (FIGS. 14A and 14B). As shown in FIG. 14A of U.S. Pat. No. 7,303,881, the ability to stimulate the expression of CD80/CD86 on DC2.4 cells by different cationic liposomes varies greatly. Lipofectamine®, a 3:1 (w/w) liposome formulation of the polycationic lipid 2,3-dioleyloxy-N-[2(sperminecarboxamido)ethyl]-N,N-dimethyl-1-propanaminium trifluoroacetate (DOSPA) and the neutral lipid dioleoyl phosphatidylethanolamine (DOPE), and liposomes prepared from O,O'-dimyristyl-N-lysyl aspartate (DMKE) and O,O'-dimyristyl-N-lysyl-glutamate (DMKD), strongly stimulated the expression of CD80/CD86 by CD2.4 cells.

As further disclosed in U.S. Pat. No. 7,303,881, the ability of different cationic lipids to stimulate the expression of CD 80 on DC 2.4 cells varied. Both hydrophilic head and the lipophilic tail of the lipids have significant effect on this ability. For example, the DXEPC lipids with the ethyl phosphocholine (EPC) head groups appear, in general, to be more potent than the DXTAP lipids with trimethylammonium propane (TAP) head group. Within the lipids bearing one particular head group structure, lipids with shorter (1,2-dilauroyl-sn-glycero-3-ethylphosphocholine (DLEPC-12:0), 1,2-dimyristoyl-sn-glycero-3-ethylphosphocholine (DMEPC-14:0)) or unsaturated (1,2-dioleoyl-sn-glycero-3-ethylphosphocholine (DOEPC-18:1)) acyl chains appear to be more potent than those with longer (1,2-dipalmitoyl-sn-glycero-3-ethylphosphocholine (DPEPC-16:0)) or saturated (1,2-distearoyl-sn-glycero-3-ethylphosphocholine (DSEPC-16:0)) acyl chains. These data however, demonstrated that multiple cationic lipids were capable of stimulating the activation of dendritic cells. Studies reported in U.S. application Ser. No. 12/049,957 highlight the mechanism by which cationic lipids act as immunostimulators.

Data from the abovementioned studies have led to the observation that the cationic lipids are not only efficient targeting and delivery vehicles for antigens to APC of the immune system, but also function as potent adjuvants under low dose composition ranges to directly influence immune system function through activation of MAP kinase dependent signaling pathways with resultant production of immune system regulatory molecules including cytokines and chemokines. A clear dose-response effect of cationic lipid on the immunostimulatory capabilities of the formulations have been demonstrated. It was demonstrated that upon receiving the lipid/antigen complex, the particles were mainly taken up by dendritic cells, the major professional antigen presenting cells. The initiation of dendritic cell activation and migration to the draining lymph node facilitates immune responses against antigen specific TC-1 tumors as demonstrated. Functional CD8⁺ T lymphocytes were generated in mice upon receiving a DOTAP/E7 injection and tumor sizes decreased and exhibited enhanced apoptosis, owing to the increasing number of infiltrating T cells in the tumor microenvironment. The resulting bell-shaped (activity decreases above and below the optimal dose) cationic lipid dose response curve demonstrated activity at very low doses, indicating that the activity of the cationic lipids as adjuvants or immunostimulators is so potent that the $EC_{50}$ is as low as about 15 mole per injection. High doses of cationic lipids eliminate the immunostimulatory activity. We have also demonstrated that when an antigen such as, for example, ovalbumin, is incorporated into the cationic liposomes and administered in a single subcutaneous injection, effective antibodies against the antigen are produced. Cationic liposomes can also induce expression of the co-stimulatory molecules CD80 and CD83 and activate human dendritic cells. It is clear that at optimal dose compositions, the cationic lipids and cationic lipid/antigen complexes in addition to effective delivery to the dendritic cells are potent activators of the immune system and provide simple, safe, and very efficient immunotherapies useful in preventing and treating diseases.

Based on an understanding of the mechanism of immunostimulation, further studies were performed to evaluate the effect of chirality in cationic lipids and the immunostimulatory capability of cationic lipids. To this effect pure synthesized R and S enantiomers of DOTAP were utilized and compared with the commonly utilized racemic mixture. Both R and S enantiomers of DOTAP were demonstrated to possess similar ability to the racemic DOTAP with regards to activation and maturation of dendritic cells. All three lipids induced dendritic cells to express the co-stimulatory molecules CD 80 CD 83 and CD 86.

An important characteristic of an immunostimulator capable of inducing cellular immune responses to disease is its ability to induce the production of critical chemokines and cytokines. As reported in the Example, significant differences were observed between the R and S enantiomers of DOTAP in their ability to induce chemokine and cytokine production. R-DOTAP was observed to be a more potent immune activator than S-DOTAP. In all cases the potency of R-DOTAP was equivalent to or higher than that of the DOATP racemic mixture.

In order to determine if the in-vitro potency in cytokine induction would translate to in-vivo therapeutic efficacy, three formulations, R-DOTAP/E7, S-DOTAP/E7 and DOTAP/E7 (racemic mixture) were evaluated for their ability to eradicate HPV-E7 positive tumors in tumor-bearing mice. Each formulation was evaluated at multiple lipid doses. As demonstrated in FIGS. 12-15, both R-DOTAP and DOTAP containing formulations exhibited a bell-shaped lipid-dose response with strong E7 specific activity leading to tumor regression within specific optimal dose ranges. S-DOTAP containing formulations did not induce tumor regression under any condition observed, although high lipid formulations slowed tumor growth.

It is therefore evident that the R enantiomer of DOTAP is responsible for the majority of the observed adjuvant effect of DOTAP. However, both enantiomers are potent activators of dendritic cells leading to maturation.

The studies reported above identify specific unique compositions and applications of cationic lipids consisting of chiral lipid or mixtures of chiral lipids, which can be exploited to develop simple, cost effective, and much needed immunotherapies for several debilitating diseases.

As various changes could be made in the above-described aspects and exemplary embodiments without departing from the scope of the invention, it is intended that all matter contained in the above description shall be interpreted as illustrative and not in a limiting sense. To that end, while the examples primarily discuss enantiomers of the cationic lipid DOTAP, those skilled in the art will recognize that this cationic lipids is merely exemplary and that the methods and mechanisms are applicable to other cationic lipids.

What is claimed:

1. A method of enhancing a DOTAP induced immunostimulatory effect in an immune system of a mammal, said method consisting of the step of administering a chiral cationic lipid consisting of R-DOTAP to the mammal.

2. The method of claim 1, wherein the immunostimulatory effect includes production of immune system regulatory molecules.

3. The method of claim 2, wherein the immune system regulatory molecules include at least one cytokine or chemokine.

4. The method of claim 3, wherein the at least one cytokine or chemokine is selected from CCL-3, CCL-4, CCL-5, CCL-19, IL-2, IL-8, IL-12, or combinations thereof.

* * * * *